United States Patent [19]

Opie, deceased et al.

[11] Patent Number: 4,947,827

[45] Date of Patent: Aug. 14, 1990

[54] FLEXIBLE ENDOSCOPE

[75] Inventors: Eric Opie, deceased, late of Brier, Wash., by Elizabeth J. Terry, executrix; Fred E. Silverstein; David R. Kreft, both of Seattle, Wash.

[73] Assignee: Opielab, Inc., Seattle, Wash.

[21] Appl. No.: 292,473

[22] Filed: Dec. 30, 1988

[51] Int. Cl.$^5$ .............................................. A61B 1/00
[52] U.S. Cl. ...................................................... 128/4
[58] Field of Search ................ 128/4, 6; 604/280, 282

[56] References Cited

U.S. PATENT DOCUMENTS

| | | | |
|---|---|---|---|
| 3,960,143 | 6/1976 | Terada | 128/4 |
| 4,277,168 | 7/1981 | Oku | 128/4 X |
| 4,646,722 | 3/1987 | Silverstein et al. | 128/4 |
| 4,676,228 | 6/1987 | Krasner et al. | 128/4 |
| 4,676,229 | 6/1987 | Krasnicki et al. | 128/4 |
| 4,726,355 | 2/1988 | Okada | 128/4 |

FOREIGN PATENT DOCUMENTS 60-1681  1/1985  Japan .

*Primary Examiner*—William H. Grieb
*Attorney, Agent, or Firm*—Seed and Berry

[57] ABSTRACT

Various methods and mechanical devices for providing manipulation and steering of the bending section of an endoscope having a sheath thereon is disclosed. In one embodiment, the longitudinal center axis of a biopsy type is aligned with the longitudinal center of the insertion tube, both being in common with the instantaneous bending center of the insertion tube. The insertion tube is capable of only right and left movement through steering but is also rotatable with respect to the handle to permit the tip to be positioned in any desired location. In an alternative embodiment, the instantaneous bending center is radially offset from the longitudinal center of the insertion tube. The hinges are positioned in the bending section of the insertion tube for locating the instantaneous center of bending at a desired location in a groove. Four, or in an alternative embodiment, three cables are provided for controlling the movement and steering of the bending section. Because the cables are not symmetrically located with respect to the instantaneous bending center, the mechanical control assembly is designed to take into account the difference between the movements of the respective cable through the full range of motions. In an alternative embodiment, the channel is located radially offset from the instantaneous center of bending and the biopsy tube assembly is made stretchable or compressible to ensure that the biopsy tube end remains aligned with the end of the insertion tube end.

41 Claims, 12 Drawing Sheets

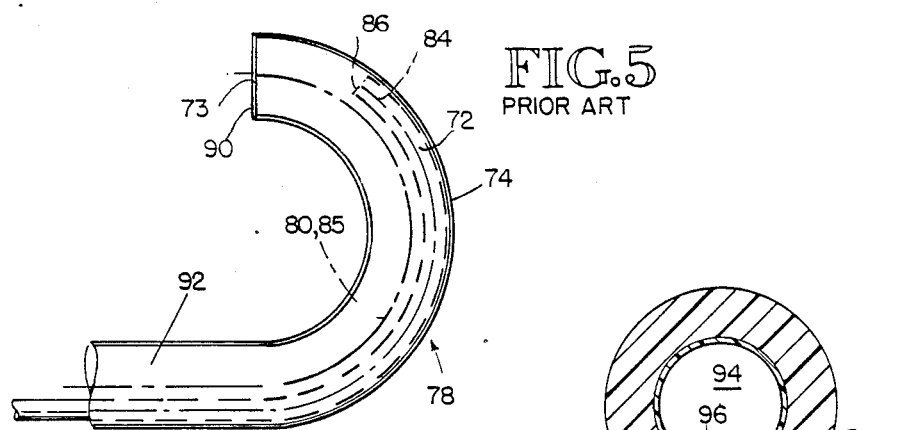
FIG. 5 PRIOR ART
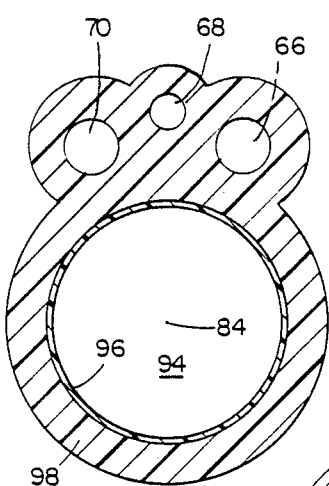
FIG. 7
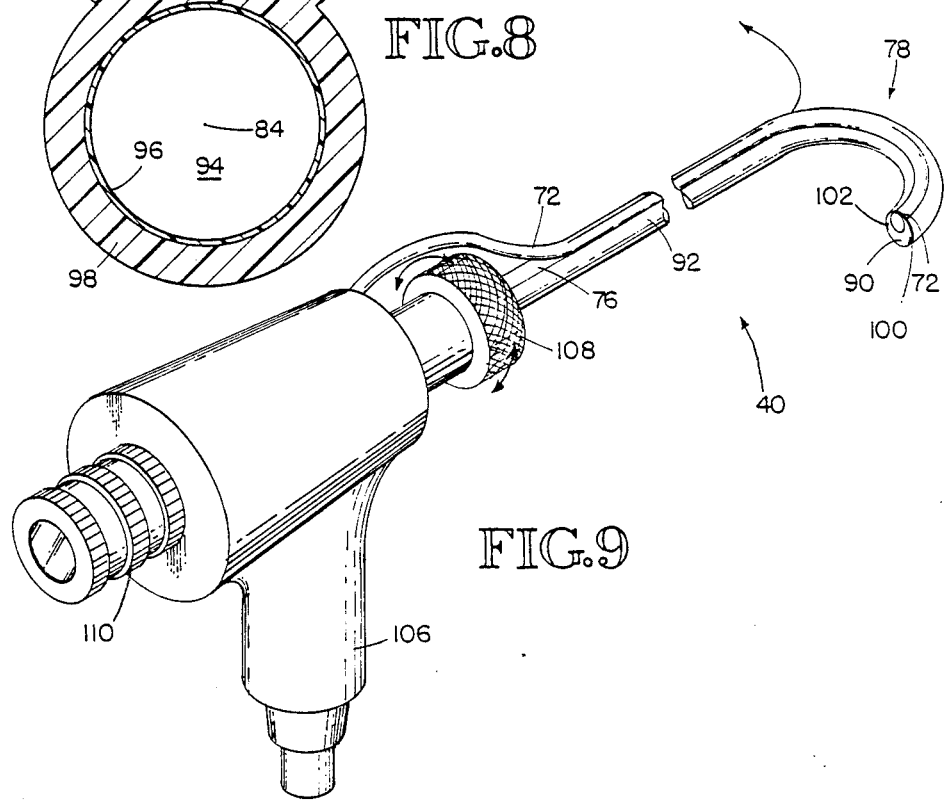
FIG. 8
FIG. 9

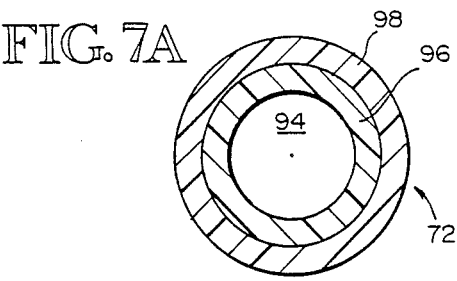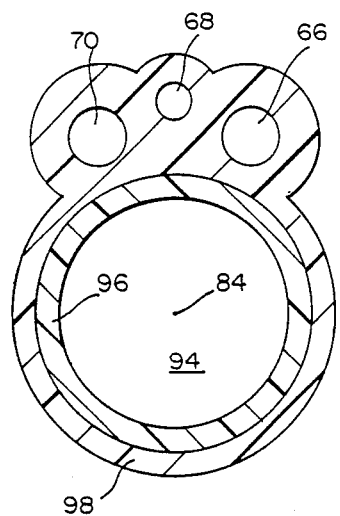

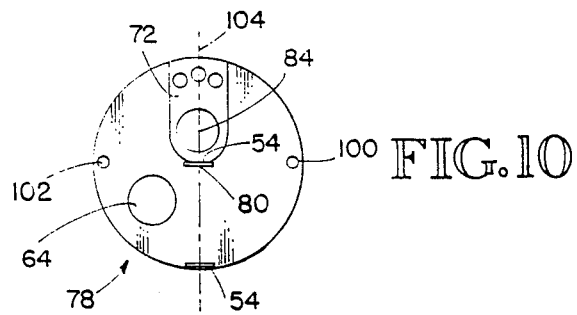
FIG.10
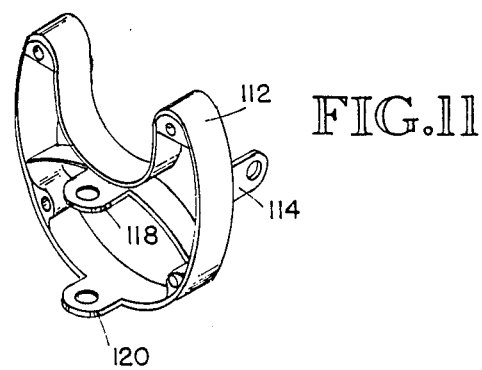
FIG.11
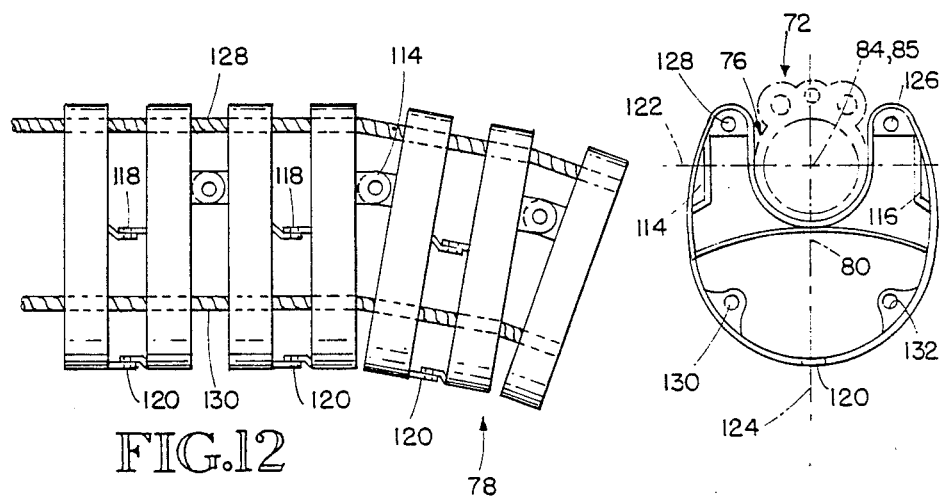
FIG.12
FIG.13

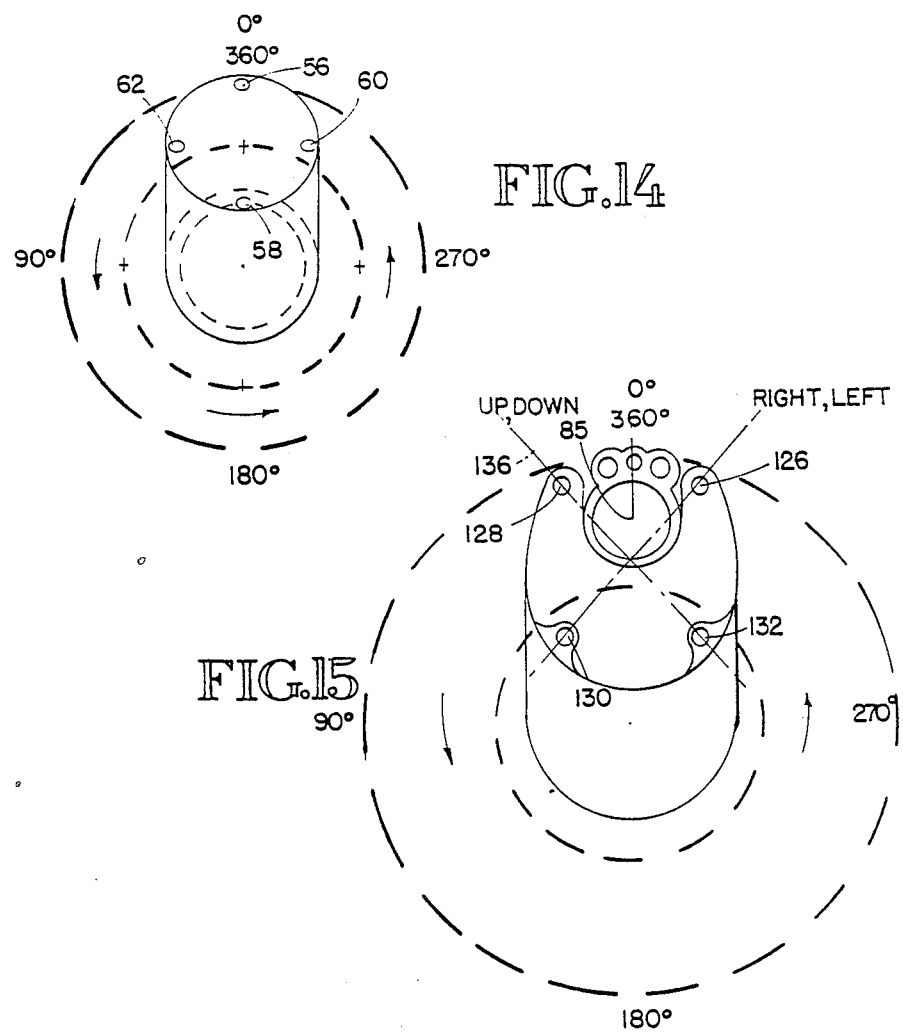
FIG. 14
FIG. 15
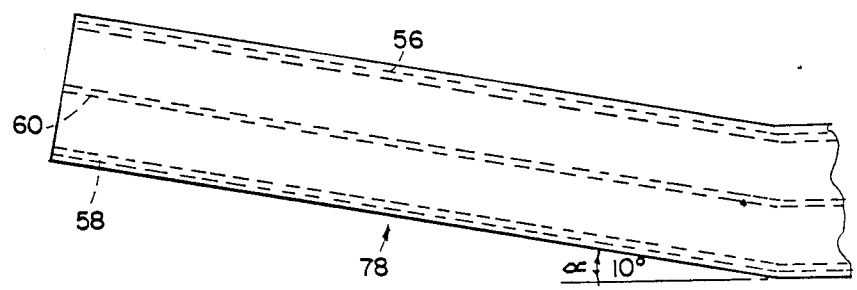
FIG. 14A

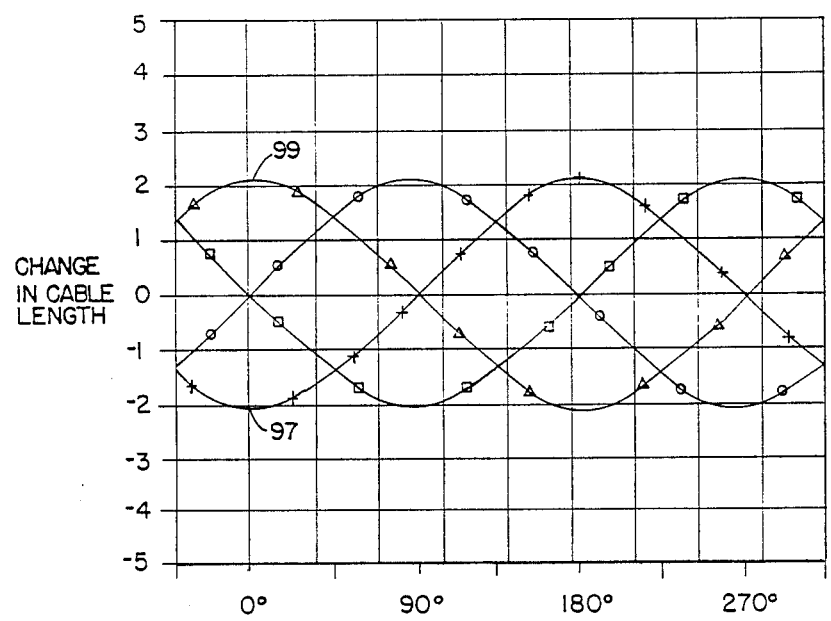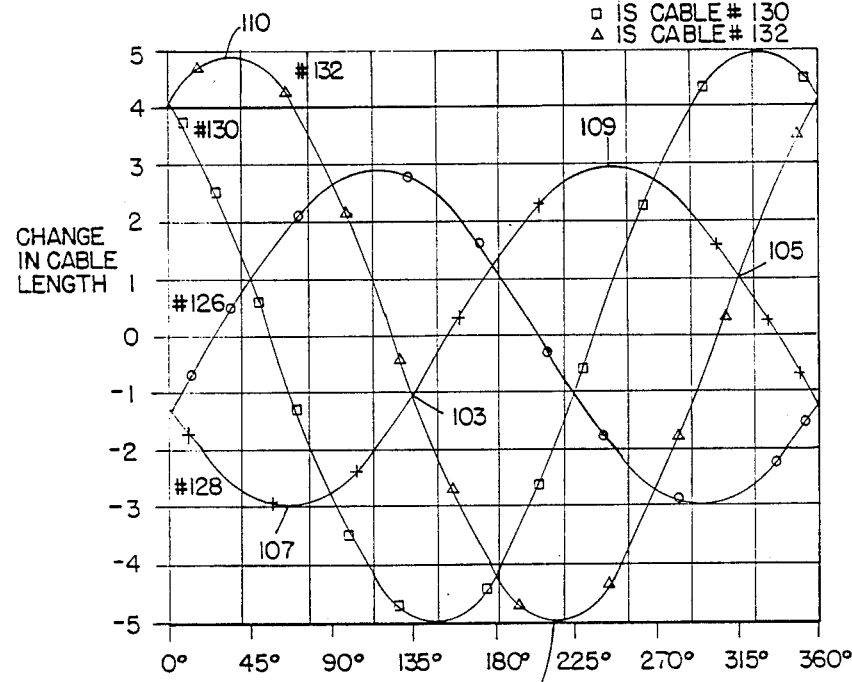

△ = ERROR CORRECTION FOR CABLES #128 & #132
□ = ERROR CORRECTION FOR CABLES #126 & #130

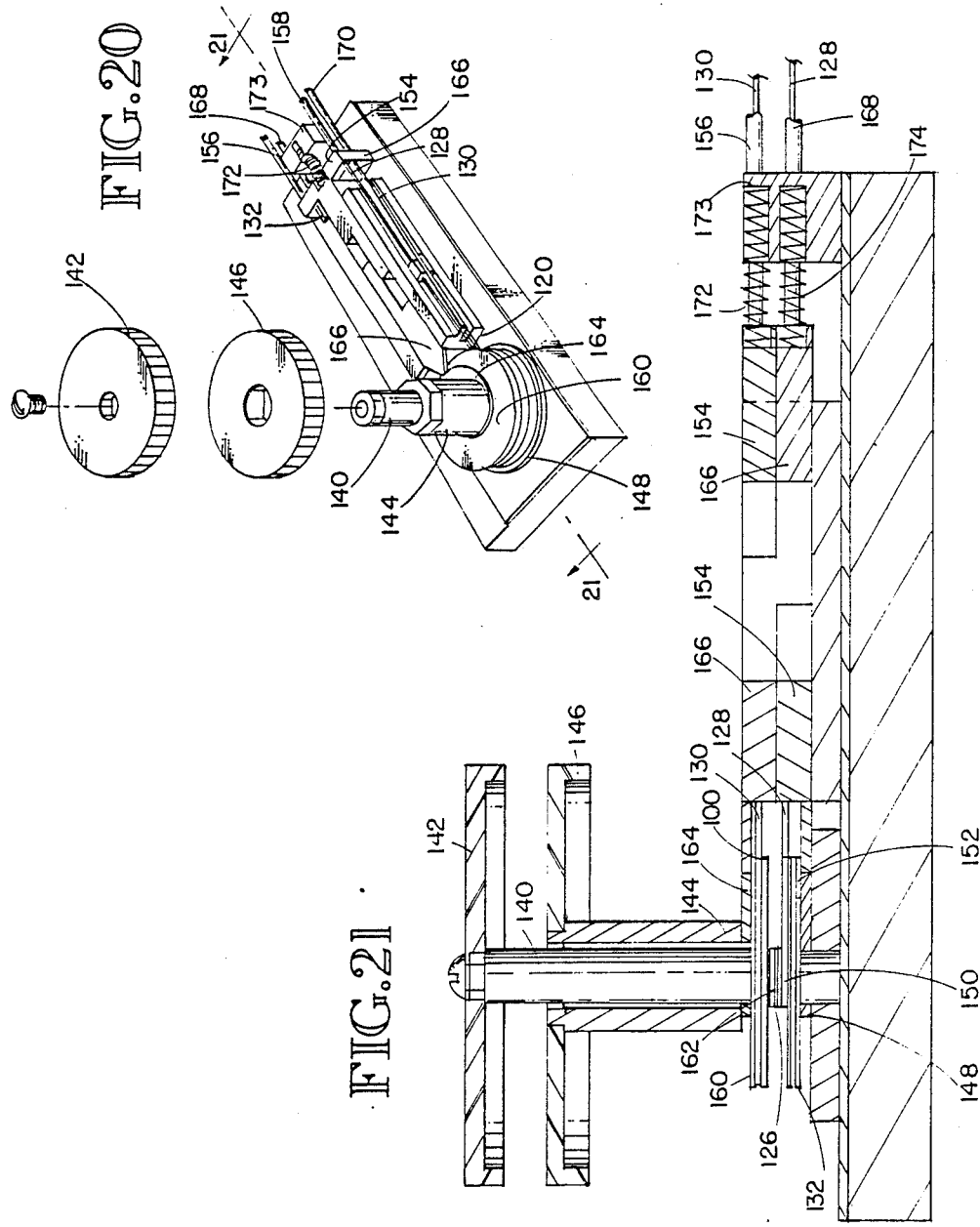

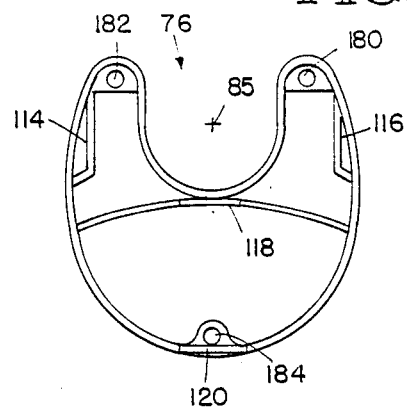
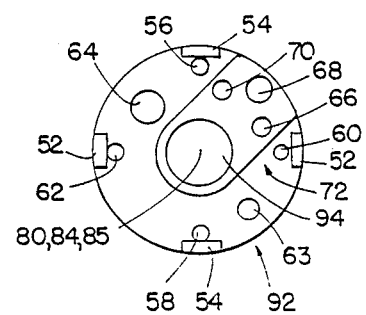
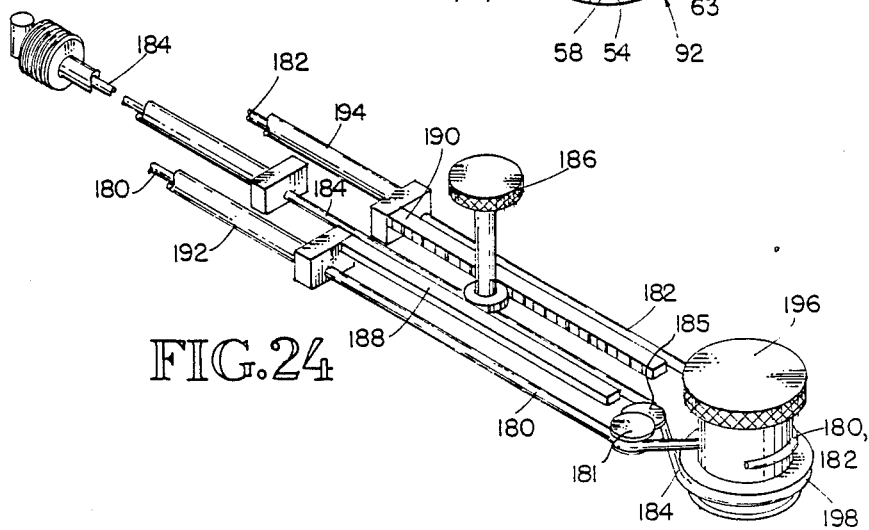

FLEXIBLE ENDOSCOPE

Technical Field

This invention relates to endoscopes, and more particularly, to the structure and method of maneuvering the bending tip section of an endoscope and various types of tubing for use within an endoscope.

Background of the Invention

Endoscopes are presently used for diagnostic and therapeutic purposes. There are many different uses for endoscopes, and frequently the endoscope design is varied, depending on its use, to optimize the performance of the endoscope for its intended purpose. For example, there are upper endoscopes for examination of the esophagus, stomach, and duodenum, colonoscopes for examining the colon, angioscopes for examining the blood vessels and heart, bronchoscopes for examining the bronchi, laparoscopes for examining the peritoneal cavity, arthroscopes for examining joint spaces, and sigmoidoscopes for examining the rectum and sigmoid colon.

Endoscopes must be very flexible to permit them to travel from the point of insertion in the body to the desired location within the human body. The tip of the endoscope must also be steerable to permit the physician to place the tip at a selected location, for examination, treatment, biopsy or the like. The endoscope may include one or more diagnostic or treatment devices such as tubings for water, air, and biopsy; a viewing device or the like. The tubings inside the endoscope must be capable of bending and flexing without kinking or collapsing as the endoscope is moved through the body. It is especially important that the biopsy tubing not collapse because forceps of a particular diameter may be required to travel along the biopsy tubing or, alternatively, particulate matter may be required to travel from the tip of the endoscope, through the biopsy tubing, into an external container for tests or removal.

Endoscopes must be adequately cleaned and sterilized in between each use on different patients to ensure that disease is not transmitted from one patient to another. The endoscope may be cleaned between each use; however, even with extensive cleaning using chemicals, such as gluteraldehyde, complete sterilization may not be ensured, particularly of the tubings within the endoscope. According to U.S. Pat. No. 4,646,722, to Silverstein et al. and incorporated herein by reference, the endoscope is kept clean and sterilized by placing a sheath over the endoscope insertion tube prior to use on each patient. In addition, the various tubings which come in contact with body fluids are disposable. A channel is provided in the endoscope into which the disposable tubings are placed. The sheath and tubings are removed and disposed of after each use and a new sheath and tubings are used to ensure that all portions of the endoscope are completely sterile prior to use on each patient.

Use of disposable tubings in an endoscope creates additional problems. The tubing must be inexpensive enough to be disposable but flexible enough for use in the endoscope and strong enough to not collapse when the endoscope undergoes significant bending in the body. The tubing must be easily removable from, and insertable into, the channel of the insertion tube of the endoscope. Tubings which are easily removable from a channel in the insertion tube may have the tendency to move relative to the insertion while in use in the patient, creating additional problems. The tubing and insertion tube must be designed to ensure that the distal end of the tubing remains aligned with the distal end of the insertion tube. Tubings used in current endoscopes are not suitable to be disposed of and replaced between use on each patient. Further, current insertion tubes are not constructed to ensure that the distal end of the disposable tubing does not move relative to the distal end of the insertion tube.

Summary of the Invention

It is therefore an object of the invention to provide tubing for placement in a groove of an insertion tube which is sufficiently economical to manufacture to permit it to be disposed of after a single use while having the required properties for tubing in an endoscope.

It is an object of this invention to ensure that the distal end of the tubing does not extend significantly beyond or withdraw from the distal tip of the endoscope even though the endoscope insertion tube may undergo significant bending.

It is another object of this invention to provide an insertion tube which is rotatable about its longitudinal axis to permit easier manipulation of the insertion tube within the body.

It is another object of this invention to provide an insertion tube having the instantaneous bending center of the insertion tube approximately aligned with the longitudinal axis of a disposable tubing within a channel groove.

These and other objects of the invention, as will be apparent herein, are accomplished by providing a disposable tubing for placement in a channel of an endoscope insertion tube. The disposable tubing is preferably an extruded plastic tubing having two different layers. The inner layer is a thin lining made of a relatively hard material and the outer layer is a thick layer made of flexible material. The inner surface is slippery but because it is quite thin, the tubing flexibility characteristics are similar to that of the outer layer.

The endoscope insertion tube is coupled to a handle which contains the controls for directing the insertion tube and diagnostic and therapeutic tools used by the physician. The insertion tube is rotatably coupled to the handle, permitting the physician to rotate the insertion tube about a longitudinal axis.

A channel is provided in the insertion tube to permit the tubing to be easily and quickly inserted into and removed from the insertion tube. If the channel center is not aligned with the bending center of the insertion tube, the disposable tubing may be a variable length tubing. For example, it may be stretchable or include pleats.

Alternatively, the tubing may be a constant length, nonstretchable tubing. If a constant length tubing is used, the longitudinal center of the channel is aligned with the longitudinal bending center of the insertion tube. The bending centers of the insertion tube and the channel may be aligned by aligning the channel with the longitudinal center of the insertion tube. Alternatively, the channel may be positioned along an outer radius of an insertion tube having a bending center aligned with the center of the channel. The insertion tube may be controlled by a four-cable system, a three-cable system, or a two-cable system.

Brief Description of the Drawings

FIG. 5 is a side elevational view of the bending section of a prior art endoscope insertion tube having the biopsy tubing along an outside radius of a bent insertion tube.

FIG. 7 is a cross-sectional view of a biopsy tubing incorporating the present invention.

FIG. 8 is a cross-sectional view of an alternative embodiment of a biopsy tubing incorporating the present invention.

FIG. 9 is an isometric view of an endoscope having an insertion tube rotatable about a longitudinal axis.

FIG. 10 is an end view of the bending section of the insertion tube of FIG. 9.

FIG. 11 is an isometric view of an individual link member having hinges asymmetrically located to provide an instantaneous bending center radially offset from the longitudinal center of the bending section.

FIG. 12 is a side elevational view of the bending section of an insertion tube having four cables and comprised of the link members of FIG. 11.

FIG. 13 is an end elevational view of the insertion tube of FIG. 12.

FIG. 14 is an end plan view of a prior art insertion tube bending section bent upward at an angle α and having dotted lines along the path it travels when rotated through 360 degrees.

FIG. 14a is a side elevational view of the bending section of an insertion tube bent by an angle α.

FIG. 15 is an end view of the bending section of an insertion tube made according to the present invention bent upward at an angle α and having dotted lines along the path it travels when rotated through 360 degrees.

FIG. 16 is a graph showing the change in cable length of each of the individual cables of the prior art bending section of FIG. 14 as it is rotated through 360 degrees.

FIG. 17 is graph of the change in cable length of each of the individual cables of the insertion tube of FIG. 15 prior to compensating for changes in cable lengths based on their position from the longitudinal bending center as it is rotated through 360 degrees.

FIG. 20 is an isometric view of a control system having compensating pulleys and cams to permit steering of the insertion tube of FIG. 12.

FIG. 21 is a cross-section view of the control system of FIG. 20 taken along lines 21—21.

FIG. 23 is an end elevational view of an insertion tube having an instantaneous bending center radially offset from the longitudinal center that is steered using three cables.

FIG. 24 is a top plan view of a rack-and-pinion system for controlling the three cables of the insertion tube of FIG. 23.

FIG. 27 is an end view of an insertion tube bending section having the center of the biopsy tubing aligned with the longitudinal center of the insertion tube.

Detailed Description of the Preferred Embodiments

Figure 1:
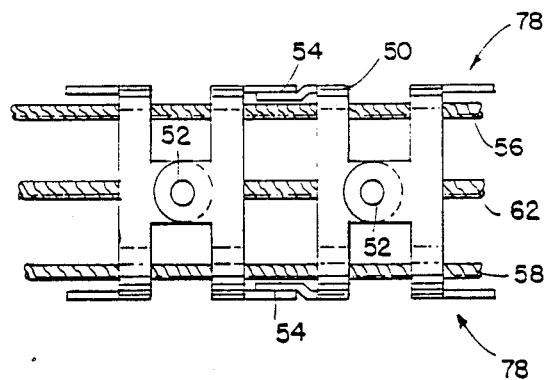
FIG. 1 is a side elevational view of a prior art insertion tube hinge assembly.

As shown in FIG. 9, an endoscope 40 includes an insertion tube 92 for inserting into the human body and a handle 106 which is held by the operator and remains outside the body. The insertion tube 92 is sufficiently flexible to permit it to travel through the interior of the human body within the selected body channel, such as a blood vessel, the esophagus, the urinary tract, the large intestine and the like. The insertion tube 92 also includes a tip portion 78 which is steerable by the operator. Steering is generally accomplished by moving the tip portion 78 up or down or left or right after the insertion tube has been advanced to the desired location. Steering the tip portion 78 of the insertion tube 92 permits the operator to place the distal end 90 adjacent a selected target, either for viewing through a fiberoptic cable, removing a sample for biopsy purposes, placing a chemical at the selected location or other medical purposes.

Figure 4:
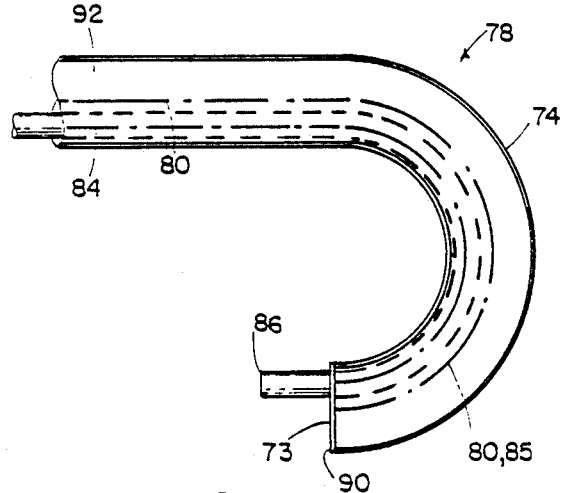
FIG. 4 is a side view of the bending tip of a prior art endoscope insertion tube with the biopsy tubing positioned on an inside radius of a bent insertion tube.

FIGS. 1-5 illustrate prior art insertion tubes of endoscopes. For some endoscopes, the tip portion 78 must be sufficiently steerable that the operator can point the distal end 90 in any selected direction in any selected orientation. Further, the tip portion, tubings and medical instruments therein must be sufficiently flexible to bend through greater than 180 degrees. The tip portion 78 of the insertion tube 92 includes a plurality of links 50 coupled together at side hinges 52 and top and bottom hinges 54. Four cables 56, 58, 60 and 62, respectively, extend from a set of controls outside of the body to the tip of the insertion tube to permit steering. Retracting a bottom cable 58 while extending a top cable 56 an equal length causes the tip portion to bend downward, as shown in FIG. 4. Conversely, extending the bottom cable 58 while retracting the top cable 56 causes the tip portion to bend upward, as shown in FIG. 5. Similarly, the endoscope tip portion 78 can be bent either right or left by retracting or extending right cable 60 and left cable 62, respectively. The distal end 90 of the endoscope can be positioned in any desired location by appropriate steering and controlling of the up/down and left/right controls, as is known in the art.

The endoscope insertion tube 92 includes a variety of medical devices. A viewing device 64, a wash channel 66, an air channel 68 and other utility channel 70 are generally provided. The viewing device may be a fiber optic cable, a ccd imager that creates electrical signals from visual input, a t.v. camera, or other known viewing devices. An ultrasonic testing probe may also be present. Electrical wires will often extend the length of the insertion tube, for coupling to the viewing device, ultrasonic transducer or the like. In many endoscopes, a biopsy channel 94 is provided for removing material from the human body at a selected location or providing medical treatment. Generally, the biopsy channel 94 is sufficiently large to permit particulate matter to travel from the distal end 90 of the endoscope 40 through the insertion tube 92 to a collection site external to the human body. The biopsy channel 94 may also be sufficiently large to permit forceps, a grabbing claw, a knife or other medical device to extend through the biopsy channel to the selected location for cutting or forcibly removing selected material from the human body. Therapeutic devices, such as balloon members, chemical treatment dispensers or the like, may also travel through biopsy channel 94.

Sterilization of the endoscope insertion tube 92 can be maintained by enclosing the entire insertion tube in a sheath 74, as taught by U.S. Pat. No. 4,646,722 to Silverstein et al. and shown in FIGS. 3 and 5. A lens 73 cap at the distal end of the sheath permits fluids and materials to enter and exit the various channels while at the same time providing a window for the viewing device and preventing external fluids from contacting the insertion tube within the sheath. Sterilization also requires that a biopsy tube assembly 72, including the biopsy channel 94 and other tubings 66, 68 and 70 that come in contact with the human body, be removed from the insertion tube and disposed of in between each use. In order to easily place and remove the disposable tube assembly 72 into and from the insertion tube, a channel 76 is provided into which the disposable tubing 72 is placed. In the prior art device of FIG. 3, the channel 76 opens into one side of the insertion tube to provide easy access.

Figure 2:
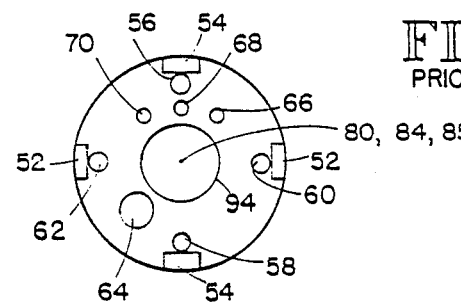
FIG. 2 is an end view of the insertion tube of FIG. 1.
Figure 3:
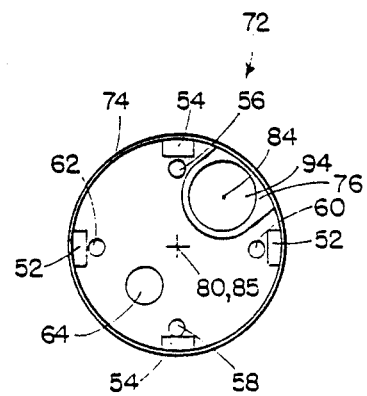
FIG. 3 is an end view of a biopsy tube positioned in a channel located off center in a prior art endoscope insertion tube.

In the prior art device as shown in FIG. 2, which did not have surrounding sheaths or removable biopsy channels, the longitudinal center 84 of the biopsy channel 94 could easily be aligned with the longitudinal center 80 of the tip portion 78. The instantaneous bending center 85 was also aligned with the longitudinal center 80. In the devices having a sheath 74, as shown in FIGS. 3-5, the channel 76 is open to one side to permit the biopsy tube assembly 72 to be removed. Because the channel 76 is shallow, the longitudinal center 84 of the biopsy tube assembly 72 is radially offset from the longitudinal center 80 and bending center 85 of the tip portion 78. U.S. Pat. No. 4,616,636 incorporated by reference also illustrates an insertion tube having grooves offset from the center.

Having the longitudinal center 84 of the biopsy tube 72 radially offset from the longitudinal bending center 85 of the tip portion 78 creates problems not previously existing in the prior art. As shown in FIG. 4, when the tip portion 78 is bent downward the biopsy tube assembly 72 is on an inside radius and travels a shorter distance around the curve than the center 80. Generally, the biopsy tubing assembly 72 is rigidly coupled to the lens cap 73. If the biopsy tubing 72 is on an inside radius, the tubing 72 may extend forward and lift the lens cap 73 off the insertion tube 92, destroying the sterile environment within the sheath 74. Alternatively, if the biopsy tubing 72 is not rigidly coupled to lens 73, the biopsy channel distal end 86 may extend out of the end 90 of the insertion tube 92 as shown in FIG. 4. Similarly, when the tip portion 78 is bent upward with the biopsy tubing 72 on an outside radius, the distal end 86 tries to retract from the tip 90 of the insertion tube 92 which may break the lens cap 73 or pull it into the channel 76 making acquisition of material difficult or impossible.

FIGS. 6a-27 illustrate various approaches for solving the problem of the disproportionate change in length between the biopsy tubing 72 and the insertion tube tip portion 78 according to the invention. A first approach is to provide a biopsy tubing which is stretchable. A second solution is to provide a groove for the biopsy tube whose length does not change as the tip portion is bent. For both solutions, the biopsy channel 94 must fulfill the criteria of being flexible yet non-kinking when bent, while being sufficiently large to provide the desired use. Because the biopsy tubing is disposable, it is also desirable to minimize the cost.

Figure 6A:
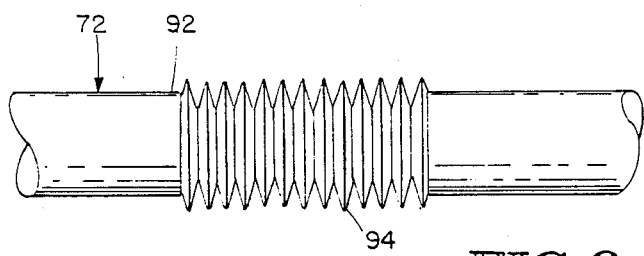
FIG. 6a is a side elevational view of a biopsy tubing assembly having pleats.

A first technique for providing a stretchable biopsy tube is shown in FIG. 6a. The walls 92 of the biopsy tube 72 may be pleated, as is presently done in curtains, folding walls and accordions. The pleats 94 can be located at the proximal end of the insertion tube where space is not a premium. The distal end 86 of the biopsy tubing 72 is rigidly fixed to the sheath 74 which is coupled to the distal end 90. Alternatively, the tubing 72 may be fixed by a hook or clasp, to the distal end 90 of the insertion tube 92 to ensure that the biopsy tubing end 86 remains aligned with the insertion tube end 90. As the insertion tube 92 is bent and steered, the pleats 94 can fold or unfold to provide the relative movement necessary between the biopsy tube 86 and the insertion tube 92. When the tip portion 78 is straight, having no bends, the pleats are at an intermediate position and have sufficient material for unfolding, that is, extending when the biopsy tube 72 is along an outside radius and sufficient space for folding, that is, contracting when the biopsy tube 72 is along an inside radius. Lubrication is provided between the tubing 72 and the channel 76 to permit the tubing to easily slide into the channel. While providing pleats 94 in the biopsy tubing 72 is a workable solution to the problem within the scope of the invention, other problems may continue to exist. For example, producing an inexpensive, disposable biopsy tube 72 having pleats may be difficult. Further, equipment, such as forceps may snag the pleats or the material being removed may contact the pleats. The pleats may interfere with the principal function of the biopsy tubing 72.

An alternative solution (not shown) is to provide a loop of biopsy tubing 72 outside of the insertion tube and exterior to the human body while fixing the end 86 of the biopsy tube 72 to the end 90 of the insertion tube 92. The loop is positioned such that any slack can be taken up in the loop as the biopsy tube turns along on inside radius. The loop contains a sufficient length of biopsy tube 72 to permit the tubing to move along an outside radius. Lubrication, such as oil, is provided between the tubing 72 and the groove 76 along the entire length of the groove 76 to permit the tubing 72 to easily move with respect to the groove.

Figure 6B:
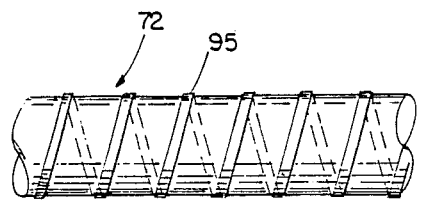
FIG. 6b is a side elevational view of a stretchable biopsy tubing assembly having a wire reinforced coil.

A third alternative approach is to provide a stretchable, reinforced biopsy tubing 72, as shown in FIG. 6b. As previously discussed, the biopsy tubing must be sufficiently rigid that it does not collapse or kink as the insertion tube flexes and bends within the human body. Generally, material which is stretchable in the longitudinal direction is subject to kinking or collapsing somewhat as it is curved or bent with respect to the longitudinal axis. A stretchable material may be used for the biopsy tubing 72 while preventing decreases in the cross-sectional area by reinforcing the tubing with a thin, flat wire coil. The major axis of the flat wire coil is parallel to the axis of the biopsy tube assembly 72. The coil 94 is encapsulated in a thin membrane of polymeric material around the outside radius of the biopsy tubing 72. The coil 94 surrounds the biopsy tube portion of the tube assembly with the air, water and other accessory channels 66, 68 and 70 exterior to the flat wire coil if desired. The reinforced design with the flat wire coil 94 provides a strong tubing assembly from a radial compressional strength standpoint that can be stretched and compressed longitudinally while being bent omnidirectionally without significant change in the biopsy tube cross-sectional structure. The biopsy tube is lubricated on its inner walls to reduce friction. The tubing assembly of FIG. 6b can stretch and compress easily without damage to the tubing or significant change in shape.

The use of a biopsy tubing 72, which moves relative to the insertion tube, requires specially designed biopsy tubings but does not require any special design for the insertion tube. The bending behavior of the insertion tube may be similar to that shown in the prior art of FIGS. 1-5 and provide a workable endoscope system. However, the tubing 72 must be relatively sophisticated and may be expensive. Further, a stretchable tubing or tubing having pleats may not have the desired design characteristics for a biopsy tube assembly.

The second approach for solving the problem of the end 86 of the biopsy tubing 72 moving relative to the end 90 of the insertion tube is to modify the bending behavior of the insertion tube 92. The structure and design characteristics of the biopsy tubing assembly 72 may be selected based on the optimal performance characteristics without having to be concerned with the stretching properties or the need to move the biopsy tubing 72 relative to the insertion tube 92. The biopsy tubing 72 may therefore be economically designed for disposability and having the properties required of the biopsy tube assembly.

Producing the biopsy tubing 72 from an extruded plastic provides a relatively inexpensive and mass producible biopsy tubing. An advantage of an extruded plastic is that a plastic can be selected which provides a slippery surface on the inner part of the biopsy tubing 72 while at the same time allowing the biopsy tubing to bend omnidirectionally about a longitudinal center. According to the principle that harder surfaces are more slick, it is desirable to have a very hard surface on the inner surface of the biopsy tubing assembly 72 of biopsy channel 94. Yet, the biopsy tubing 72 must be easily bent about a longitudinal axis 84. However, these two characteristics are somewhat mutually exclusive in some materials.

As shown in FIG. 7, to provide a biopsy tubing 72 having a slippery inner surface of the biopsy channel 94 and a flexible tubing 72, two different polymers are used to make up the biopsy tubing 72. One polymer 96 is the inner lining of the biopsy channel and a second polymer 98 is the outer casing of the biopsy tube assembly 72. The inner lining 96 is a much harder material than the outer casing 98. The inner surface is more slippery than the surface of the outer casing 98. By using a thin wall on the inner lining and a much heavier wall on the casing 98, the tubing assembly 72 takes on a flexible behavior more like the casing 98 than the harder lining material 96. With a suitable selection of materials, the hard slippery surface on the inner part of the channel 94 can be achieved with a very flexible tubing assembly 72 that will navigate the very tight bends of the endoscope tip bending portion 78. For example, the biopsy tubing assembly 72 can be an extruded plastic of PVC in two layers, the outer layer 98 being extruded on top of a previously produced and extruded inner layer 96. In one embodiment, the inner lining 96 is a 90 shore A PVC extruded tubing having a thickness of 0.01 inch and the outer casing 98 is an 80 shore A PVC extruded tubing having a thickness of 0.01. The channels 66, 68 and 70 also are lined with the harder material, the harder lining extending upward for a thickness sufficiently high that room is provided for channels 66, 68 and 70. Alternatively, the inner lining 96 is thinner, less than 0.01 and the outer layer is significantly thicker, for example, up to 0.05 if desired. The inner layer 96 is extruded first and then the outer layer 98 is extruded on top of the inner layer as is known in the art. Other materials and thicknesses may be used to provide the biopsy tube assembly 72 which optimizes the interest of having a slick inner surface and a flexible tubing assembly 72. It may be possible using the single material to provide a slick inner surface of a tubing that is sufficiently flexible to bend through greater than 180 degrees. If such a single material tubing is selected it may be used in this invention.

As shown in FIG. 8, the outer casing 98 may include small channels 66, 68 and 70 for air insufflation, water wash, waterjet or the like. Alternatively, the biopsy tube assembly may include only the biopsy channel 94 having a hard inner lining 96 and an outer casing 98, as shown in FIG. 7. A disadvantage of the use of an extruded PVC material is that the tubing 72 does not stretch or compress easily. It is therefore necessary to position the tubing 72 within the insertion tube 92 at a place that will not require stretching or compressing of the tube assembly 72.

A first technique to permit use of a disposable, nonstretchable biopsy tube assembly 72 in an endoscope insertion tube is to position the longitudinal bending center 84 of the biopsy channel 94 in line with the longitudinal bending center 85 of the insertion tube 92, as shown in FIG. 27. The groove extends from an outer surface sufficiently deep into the endoscope to position the longitudinal center of the biopsy channel 94 approximately aligned with the longitudinal center 80 and bending center 85 of the insertion tube 92. When the groove is made extremely large, other elements in the insertion tube, such as the viewing device 64, video wires, ultrasonic probe or other tools 63 must be moved to different positions to accommodate the large groove. While use of a large groove using known endoscope control mechanisms is one technique for aligning the longitudinal center 84 of the biopsy channel 94 with the longitudinal bending center 85, the shape does not optimize the cross-sectional area of the endoscope.

The second solution, namely, to provide a groove for the biopsy tube 72 whose length does not change as the tip portion is bent can be accomplished with a variety of designs, as illustrated in FIGS. 9-27. FIGS. 9 and 10 illustrate one design having a different endoscope tip portion 78 bending control from the design used in standard endoscopes. The tip portion 78 is designed to move only in a single plane, for example, right or left. The tip portion can bend only in a single plane of movement because only a single pair of cables, the cables being opposed from each other, are provided rather than the customary four cables. A right cable 100 and a left cable 102 are provided. The cables 100 and 102 are positioned equidistant from the longitudinal bending center 85 of the insertion tube bending section 78. Top and bottom hinges 54 are provided, however, side hinges 52 are not necessary. The top hinge 54 is positioned interior of the insertion tube, as shown in FIG. 10, to permit the groove to be along the central axis 104 about which hinges 54 rotate. The longitudinal center 84 of the biopsy tube assembly 72 is aligned with the axis 104 about which hinges 54 rotate to provide the bending of the tip portion 78. The instantaneous bending center 85 of the insertion tube is along exactly the same longitudinal axis as the center 84 of the channel 94. Movement to the right or left does not change the length of the biopsy tubing assembly 72 because the radius of curvature of the tubing 72 and the endoscope insertion tube are the same.

A user is limited to a single degree of freedom with the insertion tube design of FIG. 10. However, the user is accustomed to, and for some applications, may require four-direction tip control, which requires at least two degrees of freedom. According to the invention, a second plane of movement is achieved by providing rotation of the endoscope insertion tube about its longitudinal axis while holding the handle 106 stationary. FIG. 9 illustrates an embodiment of the invention wherein rotation of the insertion tube 92 is permitted about its longitudinal axis while permitting the handle 106 to remain stationary. A control member 108 is rigidly coupled to the insertion tube 92 but rotatably coupled to the handle assembly 106. The insertion tube 92 terminates in the control member 108. The coupling between the control member 108 and the handle 106 permits the control member, and thus the insertion tube to be rotated about its longitudinal axis. A simple bearing on a shaft is a suitable coupling between control member 108 and handle 106.

Because the biopsy channel 72 is relatively rigid and does not stretch or compress easily, it may be necessary for the biopsy channel assembly 72 to exit from the channel 76 prior to the rotatable coupling and then, with the appropriate length of slack, reenter the control handle or, alternatively, enter the appropriate container (not shown). The insertion tube 92 is rotatable through greater than 180 degrees in each direction, clockwise and counter clockwise to provide the full range of rotation at 360 degrees. Alternatively, the coupling may be rotatable through a full 360 degrees. Sufficient slack is provided in the biopsy tubing 72 to permit the desired rotation of the insertion tube 92 without stretching, compressing or kinking the biopsy tube assembly 72. The fiberoptic cable assembly, wires or other instruments used in the insertion tube 92 may have sufficient flexibility to rotate with the control member 108, or alternatively, they may exit from the insertion tube 92 just prior to the coupling to control member 108, similar to that shown for the tubing 72.

The user can steer the tip 90 to the right or left by rotation of knob 110 in the handle 106 and move the tip 90 to any location in a quadrant by a rotation of control member 108 while holding handle 106 stationary. Thus the combination of right and left movement of the insertion tube and shaft rotation gives the user a full range of motion while maintaining the biopsy tubing 72 a constant length relative to the insertion tube 92.

Another advantage provided by rotation of the insertion tube 92 relative to the handle 106 is the ability to acquire a target in the endoscope tip field. In current prior art devices, such as illustrated in FIG. 2, the handle is rigidly coupled to the insertion tube 92 and both must rotate as a unit. It is common for a user to see a target in the endoscope visual field and then attempt to acquire the target for medical reasons, such as to remove a sample with biopsy forceps, sytology brush, needle injection therapy or the like. However, not infrequently, the target is not in the same quadrant as the accessory as it enters from the tip 90 of the insertion tube 92. By providing a control mechanism 108 by which the insertion tube 92 is rotatable relative to the handle 106, the orientation of the tip 90 relative to the target can easily be modified. Even with current four-cable systems, a significant advantage is provided by adding a new degree of freedom for endoscope tip control, namely, right/left, up/down and clockwise/counterclockwise, as degrees of freedom without being required to rotate or change the position of the handle 106.

A third solution which permits inexpensive, extruded, nonstretchable material to be used for the biopsy tube assembly is to move the instantaneous bending radius 85 of the insertion tube 92 so that it coincides with the longitudinal center 85 of the biopsy tube assembly 72. As previously discussed with respect to FIGS. 4 and 5, if the instantaneous bending center 85 of the insertion tube 92 is different from the longitudinal center 84 of the biopsy tube assembly 72, the biopsy tube assembly 72 must grow or shrink as the bending section is curved through different radii. The growing or shrinking of the biopsy tube assembly takes place because the arc length along a longitudinal axis other than the instantaneous bending center 85 becomes longer or shorter, depending upon the direction of curvature and the distance from the longitudinal instantaneous bending center 85. By designing a tip portion bending section 78 having a longitudinal instantaneous bending center 85 aligned with the longitudinal center 84 of the biopsy tube assembly 72, the biopsy tube assembly can maintain its length irrespective of the steering or manipulation of the tip bending portion 78. More precisely, the longitudinal instantaneous bending center 85 of the insertion tube 92 is not at the longitudinal center 80 of the bending section 78, but rather, is located at the longitudinal center 84 of the biopsy tube assembly 72. FIGS. 11-13 and 23 illustrate an insertion tube tip portion bending section 78 in which the instantaneous bending center 85 of the tip portion is aligned with the longitudinal center of the groove 76 rather than the longitudinal center 80 of the insertion tube 92.

In the prior art of FIGS. 1 and 2, bending sections are typically fabricated by cascading cylindrical link elements together with hinges between them. The hinges in the prior art devices on the front of a link element are exactly 90 degrees offset from the corresponding hinge on the backside a pair of hinges are aligned with each other along their central axes, on each side as shown in FIGS. 1 and 2. The hinge elements are symmetrical about the longitudinal center 80 of the insertion tube 92 with the axes of the hinges crossing at the center 80 so that the instantaneous bending center 85 is also at the longitudinal center 80 of the insertion tube.

As shown in FIGS. 11–13, a cascade element used in a bending section 78 having an instantaneous bending center 85 radially offset from the longitudinal center 80, has one or both of the hinge sets displaced from their previous positions. A cylindrical link element of the bending section 112 includes a pair of hinges 114 and 116 on a front surface of the element 112 and a pair of hinges 118 and 120 extending from a back surface. The pivoting axis 122 for the hinge pair 114 and 116 is perpendicular to the pivoting axis 124 for the hinge pair 118 and 120. The pivoting axis 122 of the hinge pair 114 and 116 passes through the groove 76 at a desired location, such as the position of the center 84 of the biopsy tube assembly 72 when the biopsy tube assembly 72 is positioned within the channel 76. The bending axis 124 of the hinge pair 118 and 120 also passes through the groove 76 at a location approximately at the position where the longitudinal center 84 of the biopsy tube assembly 72 will be positioned. The point of intersection between the rotational axes 122 and 124 provides the instantaneous bending center of the tip portion of the insertion tube. Thus, the instantaneous bending center 85 of the tip portion 78 is radially offset from the longitudinal center 80 of the insertion tube tip bending portion 78, as shown in FIG. 13. In the design of FIGS. 11–13, the instantaneous bending center 85 is along a common axis 124 with the longitudinal center 80 of the insertion tube 92, however, this is not required according to the principles of the invention, and the instantaneous bending center 85 could be located at any convenient location with respect to the insertion tube center 80 if desired.

The endoscope cross-sectional area, as shown in FIG. 13, optimizes the shape for the insertion tube with the sheath covering the insertion tube. Preferably, prior to each use on a patient, a disposable sheath 74 is placed over the endoscope insertion tube 92 and the disposable tubing 72 is placed in the groove 76. The sheath tip includes the appropriate windows and lens cap 73 for the viewing device and seals the endoscope to maintain cleanliness of the insertion tube. The cross-sectional shape of FIG. 13 provides sufficient room for location of other tools necessary in the insertion tube other than the biopsy tubing 72, for example, a fiberoptic cable, ultrasonic probe, wiring or other devices as may be desirable.

The cables for steering and manipulating the distal end 90 are positioned near the top and bottom of the bending section, as shown in FIG. 13.

The four cables 126, 128, 130 and 132, as shown in FIG. 13, are asymmetrical with respect to the instantaneous bending center 85 of the tip bending section 78. The cables 126 and 128 are not aligned with the respective hinges 116 and 114, nor are the cables 130 and 132 aligned with the hinges. Further, the radial distance of the cables 126 and 128 from the instantaneous bending center 85 is different than the radial distance of the cables 130 and 132 from the instantaneous bending center 85. With the cables and movement of the instantaneous bending center located radially off axis from the longitudinal center of the bending section, the control motions that manipulate and steer the bending section become nonsymmetrical. Alternatively, it is possible to align the cables with the hinges as was done in the prior art, as shown in FIG. 2, and still have the bending center 85 radially offset from the center 80.

Figure 22:
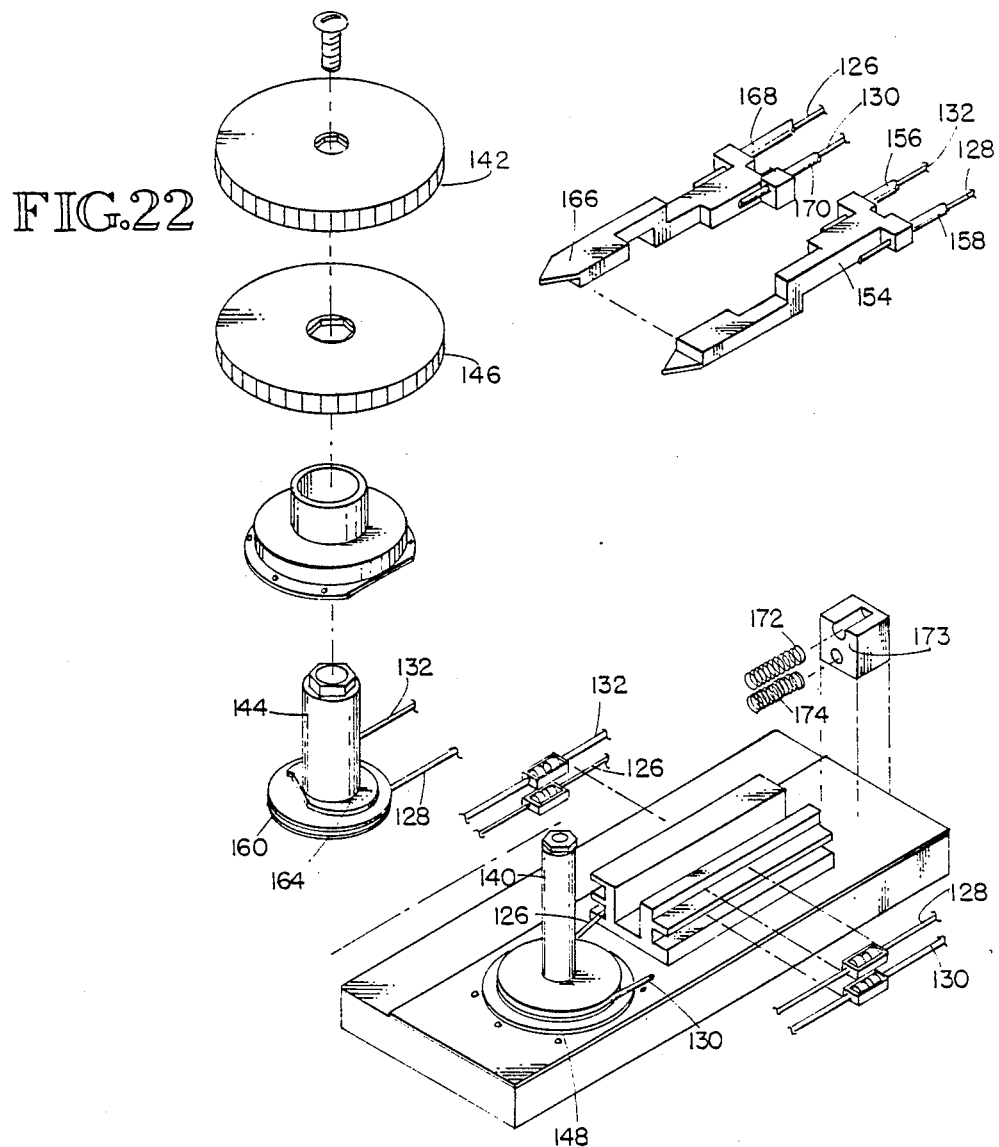
FIG. 22 is an isometric, exploded view of the control system of FIG. 20.

To accommodate for the nonsymmetrical movement of the cables and provide for accurate steering of the distal tip 90, a special set of controls is required. In designing a set of controls, it is helpful to fashion a control system that steers the distal tip in a way that mimics the feel and steering of conventional endoscopes so that the user does not perceive any change in the way the system operates, nor require additional training to operate the new system. The controls therefore as described with respect to FIGS. 20–22 are selected to provide the same feel when steering the tip as provided in conventional endoscopes in which the cables and hinges are aligned and symmetrical with respect to each other, as shown in FIGS. 1 and 2, even though none of these features are present in the bending section 78 of FIGS. 11–13.

In order to provide a control and feel similar to that provided in conventional endoscopes, a pair of opposed cables 126 and 130 control right/left plane of movement bending about the instantaneous bending center 85 and cables 128 and 132 control up/down bending plane of movement about the instantaneous bending center 85, as shown in FIG. 15. By using a combination of movements along the two planes, the tip can be placed in any desired position at a location in the human body. The right/left axis 134 is positioned radially offset from the instantaneous bending center 85. Similarly, the up/down control axis 136 does not pass through, but rather is radially offset from, the instantaneous bending center 85. Further, the cables 126 and 128 are closer to the instantaneous bending center 85 and also to the intersection of the control axis of 134 and 136 than are the cables 130 and 132, as can be seen from FIG. 15. As a result, if the tip bending portion is bent in the up direction, the cable 128 must retract a first length while the cable 132 extends a second, greater length.

It is necessary when manipulating cables 128 and 132 to steer the insertion tube bending section in the upward direction that cables 126 and 130 also retract and extend respectively to accommodate the change of motion. The relative movements of the cables are made even more complex because the up/down motion of the insertion tube bending section 78 is controlled by cables 128 and 132 rather than by cables 126 and 130. Cables 126 and 130 control the right/left bending of the insertion tube. Alternatively, it would be possible to control the up/down motion by pairing cables 126 and 128 together as a single cable opposite cables 130 and 132. The right/left motion could be provided by pairing cables 126 and 132 together opposite cables 128 and 130 if desired.

As the bending section is bent in any direction, whether up, down, right or left, each of the four control cables must grow or shrink some distance to accommodate the motion. Therefore, the up/down cables and right/left cable motions are coupled to each other. That is to say, that simple motion in the up/down direction requires the cables 126 and 132 to move even though the right/left control knob is not being manipulated by the user. The controls must therefore be designed to permit simple up/down movement by manipulating a single knob and simple right/left movement by manipulating a different knob and without requiring that both knobs be manipulated at the same time to provide desired motion even though all four cables must move.

FIGS. 14-19 aid in understanding the required relative movement of the cables with respect to each other. The retracting and extending of the cables through a full range of motions is illustrated for the prior art device of FIG. 1 and 14 in the graph of FIG. 16. Similarly, the retracting and extending of the cables for the inventive device of FIG. 15 is shown in the graph of FIG. 17.

FIGS. 14 and 14a illustrate the movement of the prior art device of FIG. 1 through a full range of motions. The endoscope bending section 78 is bent upward at an angle $\alpha$, as illustrated in FIG. 14a. The angle selected for $\alpha$ in the graphs of FIGS. 16-19 is 10 degrees. Similar plots could be made for any angle $\alpha$ from zero degrees to greater than 180 degrees. Further, the plots at a single angle $\alpha$ provide the information required to build a control system to manipulate the tip through any angle $\alpha$. After the tip portion bending section 78 is bent at an angle $\alpha$ the controls are manipulated to rotate the bending section through a full 360 degree circle maintaining a deflection from the center for a distance equal to the angle $\alpha$ as the radius of the circle through the 360 degrees, as illustrated in FIGS. 14 and 14a.

The changes in cable lengths as the prior art device of FIG. 14 is rotated through the full 360 degrees while extended outward at an angle $\alpha$ of 10 degrees from the central radius, is illustrated in FIG. 16. Retracting the cable a specific length is shown as a negative change in cable length while extending the cable is illustrated as a positive change in cable length in the FIGS. 16-19. In the graph of FIGS. 16-19, one unit is approximately 0.168 inch in length of the cable, though for different systems, it may be different. As can be seen from viewing FIGS. 14 and 16 together, when the tip is bent upward at an angle $\alpha$ and has not been rotated but remains at zero degrees, cable 56 is retracted a required distance, shown as point 97, while cable 58 is extended an equal but opposite distance, shown as point 99. The exact change in length is shown in FIG. 16. Points 97 and 99 represent the maximum excursions of the cables in the respective direction for the given angle of 2. The right/left cables 62 and 60 do not change in length but remain equal to each other and at zero change, point 101, as can also be seen viewing FIG. 16. As the endoscope insertion tube bending section 78 is rotated through 360 degrees, the individual cable lengths change through the movement. For example, as the tip begins to rotate, the length of cable 56 begins to extend from a maximum contracted position while the length of cable 58 begins to retract an equal and opposite amount. Similarly, cables 60 and 62 retract and extend equal and opposite distances from each other respectively, following the curves as shown in FIG. 16. When the tip reaches the position of 90 degrees, the cable 62 is retracted a maximum amount while the cable 60 is extended a maximum amount. Cables 56 and 58 have no change in cable length from their original, nondeflected position prior to being bent at the angle $\alpha$, the cables being exactly perpendicular to the direction of motion at 90 degrees. As the bending tip section 78 is rotated through the full 360 degrees, the pair of cables 56 and 58 always move in equal and opposite directions and lengths with respect to each other, permitting easy control by a single control rod. Similarly, the pair of cables consisting of cables 60 and 62 always move in equal and opposite directions from each other permitting control of both cables from a single control rod.

Further, the motion of cable pairs 56 and 58 is always in-phase with and independent of cable pairs 62 and 60 because their axes are perpendicular to each other and aligned with the instantaneous bending center of the insertion tube, the cables being adjacent the hinges. The in-phase relationship can be seen from FIG. 16 because the intersection between the cable lengths occurs at a zero change in cable length.

The relative change in cable lengths of the design of FIG. 15 has been plotted in FIG. 17 using the same criteria as was used for FIG. 16. Specifically, the tip portion 78 was bent upward at an angle $\alpha$, $\alpha$ being equal to 10 degrees in the example provided, and the tip rotated through 360 degrees. FIG. 17 illustrates the change in cable lengths and rotation of the tip prior to construction of a control handle for providing the symmetrical and in-phase movement of the cables. From the plot of FIG. 17 it can be seen that the cable motions are both nonsymmetrical and out-of-phase with each other. The motion of cable 128 is nonsymmetrical with respect to the motion of cable 132, the relative change in lengths being different from each other. Further, the cables 128 and 135 do not move in equal and opposite directions from each other, as can be seen because the intersections, points 103 and 105, between the cable lengths do not occur at a zero change in cable length. Unfortunately, cables 128 and 132 must act as a pair to provide the up/down steering. It is helpful if they are perceived by the user as moving both the same length as each other and in phase. Similarly, the motion of cables 126 and 130 are of different lengths and out of phase with respect to each other. For example, the cable 128, being closer to the bending center 85, moves a shorter distance than cable 135 to accomplish the same angle of bend. As shown in FIG. 17, cable 128 has a maximum excursion from zero to less than 3 units, points 107, 109, while cable 132 has a maximum excursion of about 5 units, points 111 and 113.

A control system must be designed which provides control of the endoscope of FIG. 15 while accommodating for the different changes in cable lengths and the out-of-phase relationship. One approach would be to provide an independent control rod for each of the four cables in the system, while permitting the cables to move the control rods as required when a single cable is moved. However, such a four-control rod system, while workable, is cumbersome for the user and may require additional training. Further, the optimum design is one which mimics the controls of the conventional system having a single up/down rotatable control rod and a single right/left rotatable control rod.

Use of a control system having only two control rods, rotation of which provides the desired steering of tip 90, requires the design of a new control system. The different travel lengths between the cables in a pair, such as the up cable 128 and the down cable 132 opposed to each other can be accommodated by different-sized pulleys around a single rotational control rod. However, the phase problem is significantly more difficult to solve and may not be accommodated for by different-sized pulleys. The phase errors are induced by motion on the opposing axis, therefore it is necessary to take an error function from the opposing axis and correct from one axis to the other. The up/down axis 136 extending through the center of control cables 128 and 132 is located below the instantaneous bending center 85 of the bending section 78. Similarly, the right/left control axis 134 is located below the instantaneous bending center 85. However, the axis 136 is orthogonal to the axis 134 and both are offset an equal distance radially from the bending center 85 and as a result, the error function on the left/right control cables 126 and 130 is similar in shape but offset from the error function for the up/down control cables 128 and 132. The error function would be different if the cable pairs were not located symmetrical to each other with respect to the instantaneous bending center 85 but it could still be calculated and corrected for.

The amount of error induced by coupling through the off-axis is proportional to the angle of bend and the distance from the instantaneous bending center of the bending section to the axis of the respective control cables. The length change of the respective cables is given by the equation $L = R \times \theta$, where $\theta$ is the angle of bend of the bent section 78 and R is the distance from the bending center 85. The correction needed for the cable length change can be determined from knowing the bending tip deflection angle, and the physical distance R from the instantaneous bending center 85 of the bending section and from the opposing control cable axis. Both of these parameters, R and $\theta$, are measurable for a given cable and hinge design making it possible to manufacture a controlling system that makes the appropriate corrections for each individual system.

Figure 18:
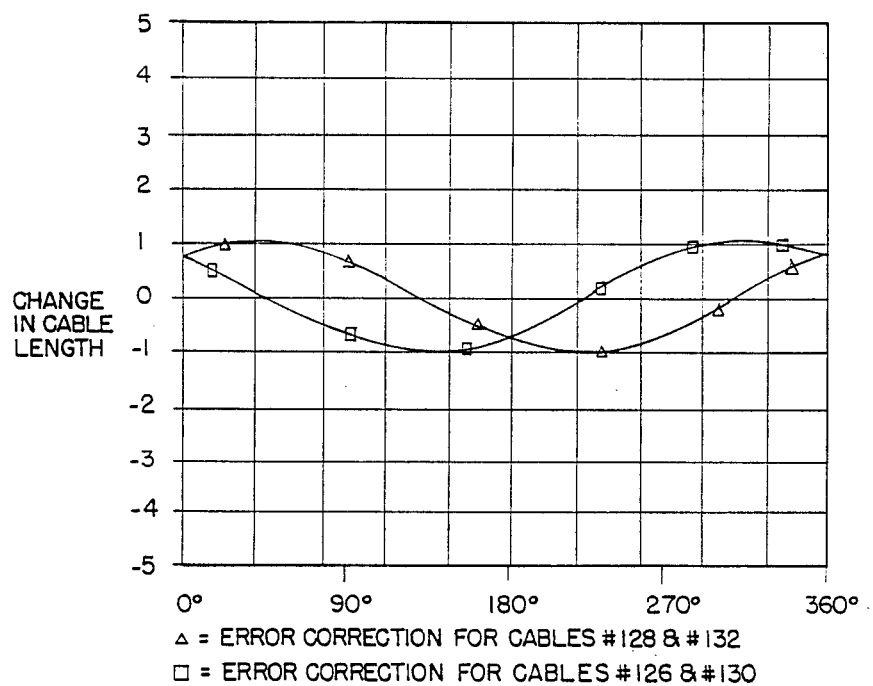
FIG. 18 is a graph of the compensation required for the changes in cable lengths of the insertion tube of FIG. 15 as it is rotated through 360 degrees.

The error function for the design of FIG. 15 has been computed and is illustrated in the graph of FIG. 18. The magnitude of the error function of cables 128 and 132 are equal to each other, as is the error function of cables 126 and 130.

Figure 19:
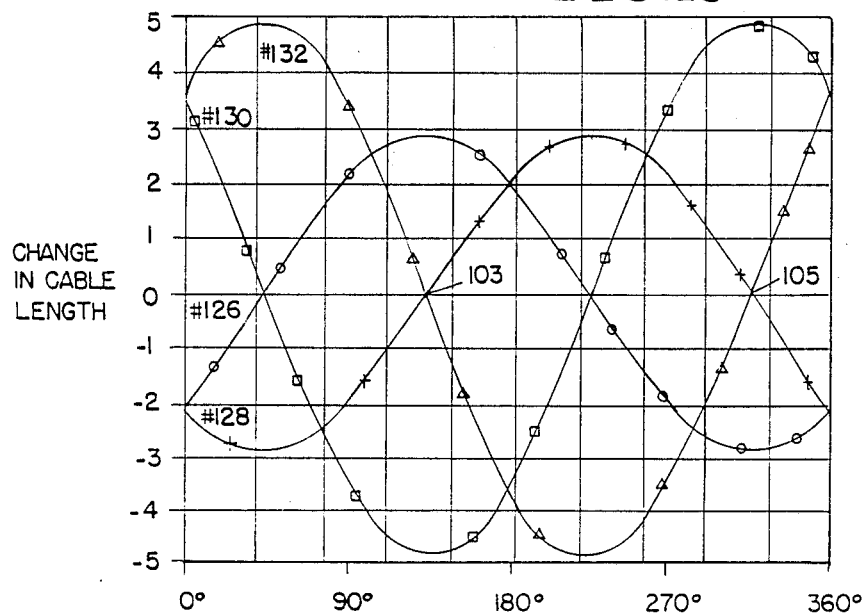
FIG. 19 is a graph of the compensated cable length changes of the insertion tube of FIG. 15 as it is rotated through 360 degrees.

The error function also accommodates for the phase relationship between the cables through the range of movement. The error function of FIG. 18 is added to the change in cable length of FIG. 17 to produce the corrected cable movement, as shown in FIG. 19. In FIG. 19, it can be seen that the phase error has been corrected because all of the intersections between opposing cables of the same pair, such as points 103 and 105, occur at zero change in cable length.

A mechanical system that provides the respective cable movement, as shown in FIG. 19, is illustrated in FIGS. 20–22a. A control rod 140 having a knob 142 attached thereto controls the right/left bending movement of the insertion tube tip portion 78 and thus control cables 126 and 130. Control rod 144 having knob 146 coupled thereto controls the bending of the insertion tube tip portion 78 in the up/down direction and thus control cables 128 and 132. Control rod 140 is centrally disposed within a shaft of control rod 144 to provide compact and convenient operation of the device. However, the control rods could be separately located if desired.

The control rod 140 includes a large-diameter pulley 148 and a small-diameter pulley 150 and a cam 152. Cable 126 is coupled to the small-diameter pulley 150 and cable 130 is coupled to the large-diameter pulley 148. Rotating control rod 140 causes the cables 126 and 130 to retract or extend respectively in opposite directions, the cables being wound opposite directions from each other around the respective pulleys 148 and 150. Further, rotating the shaft 140 through a particular angle causes the cable 130 to move a greater distance than the cable 126 because the cable 130 is coupled to a larger-diameter pulley 148.

The different diameter pulleys and movement in opposite directions are required as previously described with respect to FIGS. 12–19. Specifically, when moving in the right/left direction, the cable 126 has a change in length less than the change in length of the cable 130 because the cable 126 is closer to the instantaneous bending center 85 of the bending tip than is the cable 130. Further, the cables must move in opposite directions from each other, with one retracting while the other extends and vice versa in order to provide the required movement. The exact diameter of the pulleys 148 and 150 required to accomplish the desired movement of the cables relative to each other depends upon the exact dimensions of the insertion tube 92 and can easily be determined for a particular insertion tube 92 by measuring the respective differences from the instantaneous bending center 85 and using the principles described herein and illustrated in the graph of FIG. 19. The control rod 140 is constructed to provide the required movement and having the correctly sized pulleys 148 and 150 thereon to steer the tip portion 78 in the right/left direction as controlled by a user turning knob 142.

Cam 152 on control rod 140 is followed by a cam follower 154. The cam follower 154 is rigidly attached to the cable housing 156 and 158 of the up/down cables 128 and 132.

The cam follower 154 is in contact with cam 152 below the pulley 148 and rigidly coupled to the housings 156 and 158 which surround cables 128 and 132, which are above cables 128 and 132. Therefore, the cam follower must extend above the paths of the cables 126 and 130 to be aligned with the paths of the cables 128 and 132 which run through housings 156 and 158, respectively. The cam follower 154 bends upward at a central portion, as best shown in FIG. 22.

As previously discussed, movement of the right/left cables 126 and 130 causes an error function in the up/down cables 128 and 132 because of their coupling, as shown in FIGS. 17 and 18. It is necessary to correct the movement of cables 126 and 130 in cables 128 and 132. The cam 152 coupled to control 140, the right/left control, the and cam follower 154 coupled to the cable housing of the up/down cables provides the correction factor from the right/left control rod to the up/down cables. The cam follower moves the cable housings 156 and 158 relative to the cables 128 and 132. As is well known in the mechanical fields, movement of a cable while holding a housing stationary is equivalent to movement of the housing while holding the cable stationary. Cables 126 and 128 are moved by control rod 140. The cam 152 is coupled to control rod 140, but the cam follower 154 is coupled to the housing of the cables. The cables 156 and 158 thus move independent of the cables 128 and 132, which cables are moved by control rod 144. Rotation of rod 140 not only moves cables 126 and 128 but also corrects for the effect of their movement by the other cables 128 and 132 moving cable housings 156 and 158. Rod 144 need not rotate for the correction to be effective and is not affected by movement of the housings.

The exact shape of the cam 152 can be determined from the measurement equations previously described. The slope of the cam is such that, for any given control axis rotation, the cam height at that point is equal to the correction required for the opposing axis. For example, the height, that is the diameter of the cam 152 at any point, is equal to that additional distance required to correct the movement in the opposing axis, the up/down axis 136. The cam height at any known control rod position is determined because the linear relationship between the cable movement, changes in length, and the angle of deflection, $\theta$, with the instantaneous bending center located a distance R from the respective control axis. The angle of the deflection $\theta$ is also proportional to the angle of rotation by the control rod, by a known scale factor. With these parameters taken into account, it is possible to design a cam shape which directly and exactly corrects for the movement of the opposing cable motions. In the design as shown and described in FIGS. 20-22a, the exact correction required does occur. The correction is provided by movement of the cable housings by the cam follower 154 relative to the cables rather than movement of the cables themselves.

Accomplishing error correction by moving the housing of the opposing cable provides the same result as moving the cables with the additional advantage that the control rod to which the cables themselves are directly attached is not moved. Each control rod is capable of motion independent of the other control rod.

The up/down control rod 144 is rigidly coupled to a large-diameter pulley 160, a small-diameter pulley 162, and a cam 164. The up cable 128 is coupled to the small-diameter pulley 162 and the down cable 132 is coupled, wound in the opposite direction to the large-diameter pulley 160. Rotation of control rod 144 causes the cables 128 and 132 to move in opposite directions and different path lengths than each other because of the different diameter pulleys. The required path length is easily determined based on the dimensions of the insertion tube, as previously described with respect to FIG. 19. Cam follower 166 is in contact with and follows the contour of cam 164 as the control rod 146 is rotated. Cam follower 166 extends from the cam 164 to the housings 168 and 170 for the right/left cables 130 and 126, respectively. The cam follower 166 bends downward and meshes with the cam follower 154, as best shown in FIG. 22. Cam followers 154 and 166 are shaped to permit each of them to move independent of the other without contacting each other even during the most extreme movements of each.

Figure 22A:
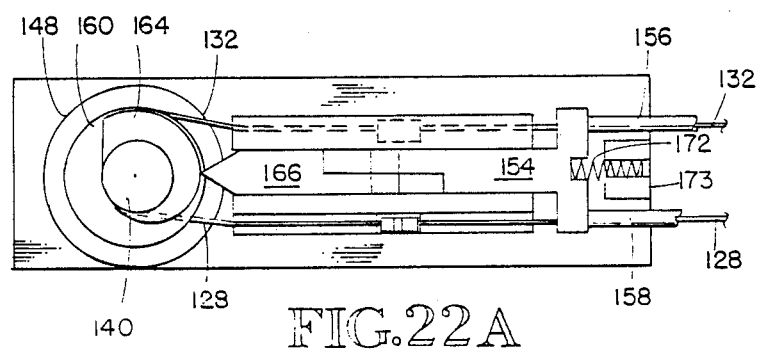
FIG. 22a is a top plan view of the control system of FIG. 20.

The design of cam 164 is shown in FIG. 22a and is identical to the shape and design of cam 152, though they are radially offset from each other. The design of cam 164 is determined using the same principles described with respect to cam 152. For the particular design shown in FIGS. 11-13, the shape of cam 164 is identical to the shape of cam 152 though they may have different shapes.

The operation of the up/down control rod 144 is similar to the operation of the right/left control knob, as previously described, and need not be repeated in detail. In summary, rotating the control rod 144 causes the up/down cables 128 and 132 to retract and extend in opposite directions and for different lengths than each other, as shown and described in FIG. 19. Simultaneously, the cam 164 also rotates, is followed by cam follower 166 which moves the cable housings 168 and 170 coupled to the right/left axis cables 130 and 126. Correction for the movement of cables 128 and 132 is thus provided to the cables on the opposing axis without effecting the cables themselves of the rod 140 which controls the cables.

Springs 172 and 174 abutting block 173 are provided to bias respective cam followers 154 and 166 against their respective cam surfaces springs 172 and 174 to ensure that the cam follower accurately follows the cam surface through its entire rotation.

Using the control mechanism as illustrated in FIGS. 20-22a, the four-cable system, as shown and described in FIGS. 11-13, can be manipulated and steered through any desired range of motion or angular deflection. Using the principles described herein for the four-cable system and the control mechanism, the appropriate control mechanism can be designed for any given bending section with four cables given the hinge and cable locations. The insertion tube assembly can therefore be designed based on the optimal cross-sectional shape without concern for the requirement of a symmetrical shape about a central axis or the need for placing hinges symmetrically with respect to each other. Further, the instantaneous bending center of the tip portion 78 can be located at any desired longitudinal axis offset radially from the longitudinal center of the insertion tube, if desired. Alternatively, the cables can be placed symmetrically about the bending center 85 while using hinges in a link member offset from each other as described with respect to FIG. 11. The cables thus positioned would be symmetrical, could move equal and opposite direction but the bending center 85 would be radially offset from the longitudinal center 80 because of the location of the hinges and intersection of their axes.

In an alternative embodiment illustrated in FIG. 23, three cables are used to control the bending section in the tip portion 78 of the insertion tube 92. In a three-cable system, the hinges may be located in exactly the same positions as in the four-cable system, if desired. Alternatively, the hinges may be located at any desired location to provide an instantaneous bending center 85 at a desired position. In the embodiment shown in FIG. 23, the axis of rotation through hinges 114 and 116 defines the axis about which up/down movement occurs and the axis that extends through hinges 118 and 120 defines the axis about which right/left movement occurs.

To provide up/down directional control, cables 180 and 182 located on either side of the groove 76 move in unison. For example, the cables 180 and 182 are retracted while cable 184 is simultaneously extended to steer the tip upward. Similarly, cable 184 is retracted while cables 182 and 180 are extended to steer the bending section downward. Because cable 184 is located further from the longitudinal instantaneous bending center 85 than cables 180 and 182, cable 184 must move a greater distance, whether retracting or extending, than the cables 180 and 182.

The right/left direction of movement is provided by retracting and extending the respective upper cables 180 and 182 while maintaining cable 184 the same length. The cables 180 and 182 are located exactly the same distance as each other from the instantaneous bending center 85 and therefore they will move equal, but opposite, distances from each other in providing the right/left motion. The common movement of the cables 180 and 182 provides for the up/down movement and the difference in movement between cables 180 and 182 provides for the right/left directional movement. The lower cable is only responsible for up/down movement and stabilizing the tip for right/left movement.

At least two mechanical assemblies are easily capable of providing the required movement of the cables with respect to each other in the three-cable system. Because the cables 180 and 182 are located equidistant from the instantaneous bending center 85, a different diameter pulley is not required. Further, because cable 184 remains stationary when cables 180 and 182 are moving with respect to each other, error correction between cable 184 and cables 180 and 182 is not required.

A first suitable control assembly for the three-cable system is illustrated in FIG. 24. A rack-and-pinion assembly coupled to the housing of the cables in combination with a control rod coupled to all three cables is a suitable mechanical assembly for providing the required steering of the insertion tube in any given direction. A rack-and-pinion assembly including a control rod 186 coupled to respective right and left racks 188 and 190 provides the right/left difference movement between the cables 180 and 182. Rotating the control rod 186 causes the racks 188 and 190 to move in equal and opposite directions from each other. The racks 188 and 190 are coupled respectively to the housings 192 and 194 of cables 180 and 182, respectively. As previously discussed, movement of the housing with respect to the cable provides the identical movement as movement of the cable within the housing. Rotating control rod 186 in a clockwise direction causes the bending tip section to turn a first direction, to the right for example, and rotating the control rod 186 in the opposite direction causes the bending tip section to be steered to the opposite direction, left, for example. The racks are made sufficiently long to permit the tip portion 78 to bend any desired angle, greater than 180 degrees if desired, the change of length about rod 186 of the racks being proportional to the degree of bend in the tip 90. The position and length of cable 184 is not affected by the rack-and-pinion assembly nor by rotation of control rod 186.

Control rod 196 provides the up/down movement. Cables 180 and 182 move an equal distance to each other in the same direction to provide the up/down directional steering. Cable 184 moves in the opposite, direction, for a greater distance than the cables 180 and 182 for the corresponding up/down steering movement. Cable 180 bends around pulley 181 and then is coupled to rod 196. Cables 180 and 182 are both wrapped in the same direction around control rod 196 such that rotation of control rod 196 causes both of the cables to retract or extend equal distances in the same direction. Cable 184 extends around a pulley 185 and then around pulley 198 which is coupled to the control rod 196. Because the pulley 198 has a larger diameter than control rod 196, rotation of the control rod 196 causes the cable 184 to be moved a greater distance than the distance moved by cables 180 and 182 for the same angular motion of rod 196. Further, because the cable 184 is wrapped in the opposite direction, it is retracted while cables 180 and 182 extend, and vice versa, for a given rotational movement of rod 196.

Figure 25:
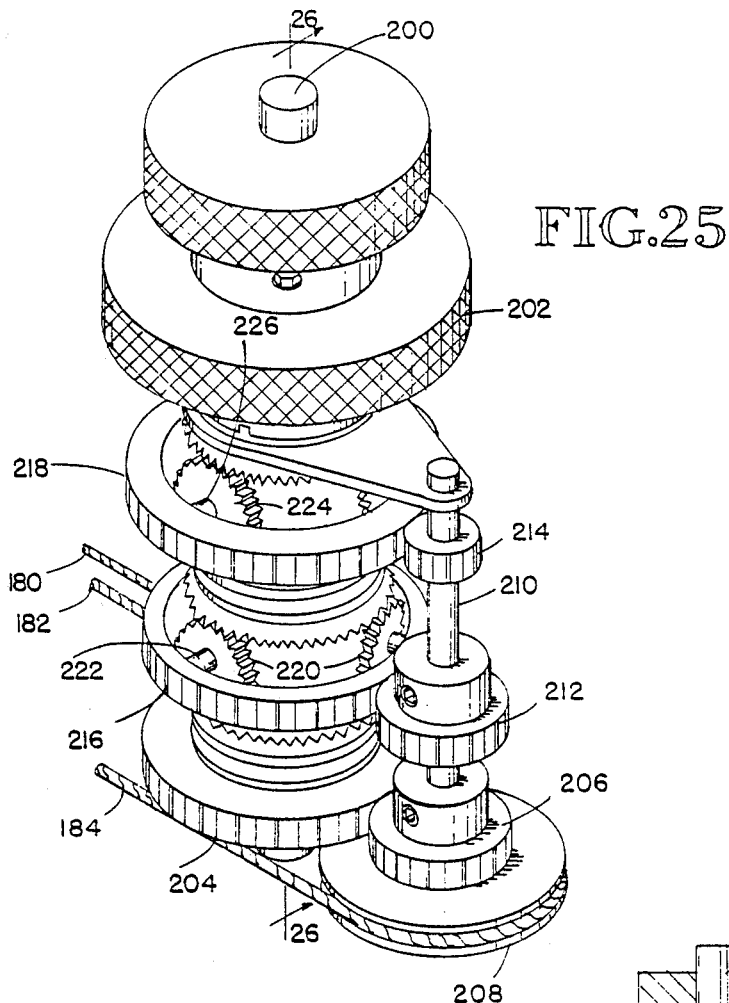
FIG. 25 is an isometric view of a gear system for controlling the three cables of the insertion tube of FIG. 23.
Figure 26:
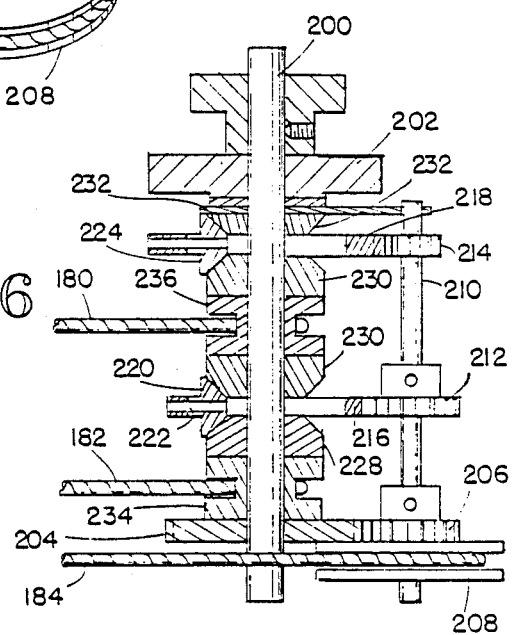
FIG. 26 is a cross-sectional view taken along lines 26—26 of FIG. 25.

An alternative mechanical assembly providing control of the three-cable system is illustrated in FIGS. 25 and 26. The control assembly includes a plurality of gears coupled to each other in the relationship required to retract cables 180 and 182 in equal lengths to each other in the same direction while extending cable 184 in an opposite direction for a greater length to provide up/down direction steering. The gears also provide for pulling cables 180 and 182 in opposite directions for an equal length while holding cable 184 stationary to provide right/left directional steering.

While numerous gear systems could be designed and built to provide the required motion, a preferred gear assembly which provides the required motion is illustrated in FIGS. 25 and 26. A control rod 200 which controls the up/down movement is rigidly coupled to a gear 204. Control rod 202, which provides the right/left movement, is rigidly coupled to a plurality of gears which are connected to pulleys having cables 180 and 182 connected thereto. The control rod 202 and associated gears are a floating gear system around control rod 200.

Rotating control rod 200 causes gear 204 to rotate which rotates gear 206. A pulley 208 is rigidly coupled to gear 206. Cable 184 is rigidly coupled to pulley 208 such that rotation of control rod 200 causes cable 184 to retract or extend a length based on the amount of rotation. Gear 206 is rigidly coupled to transmission rod 210 having gears 212 and 214 coupled thereto. Gears 212 and 214 are coupled to ring gears 216 and 218, respectively. Bevel gears 220 are coupled to ring gear 216 through pins 222. Bevel gears 220 are rotatable about pin 222. Similarly, bevel gears 224 are coupled to ring gear 218 through pin 226. Cylindrical gears 228 and 230 are coupled to bevel gear 220. Cylindrical gears 230 and 232 are coupled to bevel gear 224. Cylindrical gear 228 is rigidly coupled to pulley 234 to which cable 182 is rigidly attached. Similarly, gear 230 is rigidly coupled to pulley 236 to which cable 180 is rigidly attached. Ring gear 218 is larger in diameter than ring gear 216, therefore, the gears driving the respective ring gears, namely, gears 212 and 214, are different diameters than each other to ensure that the pulleys 236 and 234 are rotated the same linear distance at all times. In one embodiment, gears 204 and 216 are 1.0416 inches in diameter, gears 206 and 212 are 1.5208 inches in diameter, gear 214 is 0.312 inch in diameter and gear 218 is 1.250 inches in diameter.

Rotation of rod 200 rotates gear 204 which rotates gear 206. Similarly, rotation of ring gear 218 by gear 214 causes bevel gears 224 to rotate which rotates gear 230 to rotate pulley 236 and retract or extend cable 180. Gear 232 is held stationary and knob 202 does not rotate. All of the rotation of gear 218 is transferred to bevel gears 224 which rotation is transferred to gear 230 and hence to pulley 236. The pulley 236 will rotate at twice the rate as ring gear 218 because gear 232 does not rotate. All of the rotation of ring gear 216 is transferred to pulleys 234 and 236 through gears 228 and 230. The bevel gears 220 do not rotate because gears 230 and 228 are moving the same rate in the same direction as each other. Pulleys 234 and 236 rotate at the same rate because the, gear ratio from 212 to 216 is 2:1 and the gear ratio from 214 to 218 is 4:1. Even though the gears 230 and 228 are travelling at twice the rate of ring gear 218, because the gear ratio between 214 and 218 is smaller than from gear 212 to gear 216, gear 218 is only being driven at half the rate that gear 216 is being driven. When the movement originates through transmission rod 210 to gears 212 and 214, respectively, the pulleys 236 and 234 rotate in the same direction as each other to move cables 180 and 182 in the same direction while cable 184 moves a different length in the opposite direction. Control rod 202 is floating with respect to control rod 200 and the motion of bevel gear 224 is transferred to gear 230 rather than to control rod 202, permitting control rod 202 to remain stationary and isolated from the up/down motion caused by rotating control rod 200.

Rotating control rod 202 provides right/left steering of the bending section of the insertion tube as follows. Rotating control rod 202 coupled to gear 232 causes bevel gear 224 to rotate. Ring gear 218 does not rotate, but rather, remains stationary because bevel gear 224 is pinned about pin 226 for free rotation about an axis perpendicular to ring gear 218. However, rotation of bevel gear 224 causes rotation of cylindrical gear 230 and corresponding rotation of pulley 236. Cylindrical gear 230 is coupled at its other end to bevel gear 220. Bevel gear 220 is pinned about pin 222 through ring gear 216. Ring gear 216 does not rotate because bevel gear 222 rotates about cylindrical pin 222. Gear 228 is caused to rotate by the rotation of bevel gear 220, however, gear 228 rotates in an opposite direction from gear 230. Because gears 230 and 228 are the same size as each other, as are pulleys 236 and 234, cables 180 and 182 move equal lengths but in opposite directions as control rod 202 is rotated. Further, because the ring gears 216 and 218 do not rotate the cable 184 remains stationary and does not change length as gears 230 and 228 move in opposite direction from each other. Control rod 202 therefore provides right/left motion of the bending section of the insertion tube tip portion 78. The rotation of control rod 202 does not interfere with the rotation of control rod 200. The rods may be rotated independent of each other or simultaneously, in the same or opposite direction to provide the desired movement and steering of the tip portion 78 of the insertion tube.

While the control rods have been described as providing the required motion by rotating, they could provide a similar motion by linear movement, with levers and the like in place of gears. The inventions as described herein are designed to be used with an insertion tube covered by a sheath and having disposable biopsy tube assembly 72 in a channel of the insertion tube. The various control assemblies described herein thus provide many techniques for controlling the bending section of an insertion tube while providing a channel from which the biopsy tube assembly may be easily removed or placed therein. The biopsy tube 72 described with respect to FIGS. 7 and 8 and the various mechanical control systems described in the other figures may also be used in an endoscope not having a sheath 74 surrounding the insertion tube.

If desired, endoscope insertion tubes may be designed having hinges which provide for an instantaneous bending center at any given point, different than the longitudinal center of the insertion tube. The cables may be located at any desired location and controlled using the principles described herein to provide control of the insertion tube. While particular embodiments have been described to illustrate the operation of the invention, many equivalent devices could be designed which operate in the same way to provide the same result and fall within the scope of the invention.

We claim:

1. An endoscope comprising:
    an insertion tube for inserting into a human body;
    a handle coupled to said insertion tube, said handle remaining outside said human body, said insertion tube being rotatably coupled to said handle for rotation about the longitudinal axis of said insertion tube;
    a tubing extending from a tip portion of said insertion tube, exiting at an end region of said insertion tube and entering said handle; and
    a control member means for permitting a user to selectively rotate said insertion tube about its longitudinal axis while maintaining said handle in a stationary position.

2. The endoscope according to claim wherein said insertion tube is rotatable through approximately 180-degrees in the clockwise and counter clockwise directions from a position of 0-degrees with respect to the handle.

3. The endoscope according to claim 1 wherein said channels are removably coupled within said insertion tube and includes means for coupling said tubing to a tip portion of said endoscope and placing said tubing within an insertion tube of said endoscope.

4. The endoscope according to claim 1 wherein said insertion tube has an instantaneous bending center which is radially offset from its longitudinal axial center.

5. The endoscope according to claim 1 wherein said handle includes controls for steering said tip portion of said insertion tube for placement of said tip at a selected location within said body.

6. An endoscope comprising:
    a handle;
    an insertion tube coupled to said handle;
    tubing means within aid insertion tube extending from a region adjacent said handle to a tip portion of said insertion tube for transporting matter to and from said tip portion of said insertion tube, the length of said tubing being variable from a first length to a second length;
    means for fixing an end of said tubing adjacent an end of said insertion tube; and
    means for permitting at least a portion of said tubing to move relative to said insertion tube while maintaining said handle in a stationary position.

7. The endoscope according to claim 6 wherein said tubing is stretchable.

8. The endoscope according to claim 7 further including a wire coil means extending circumferentially around said tubing for preventing said tubing from decreasing in cross-sectional area when stretched.

9. The endoscope according to claim 6 wherein the outer walls of said tubing include pleats that are folded upon themselves along a portion of the length thereof when said tubing is a first length and said tubing is extended to a second, longer length by unfolding said tubing.

10. An endoscope comprising:
    an insertion tube for inserting into a human body; said insertion tube having a longitudinal central axis, and a longitudinal bending axis, the longitudinal bending axis being radially offset from the longitudinal central axis;
    a handle coupled to said insertion tube; and
    controlling means for steering a tip portion of said insertion tube.

11. The endoscope according to claim 10 wherein said insertion tube includes a plurality of link members hingedly coupled to each other by a first and second set of hinges, the axis of rotation of said first set of hinges and the axis of rotation of said second set of hinges crossing at a point radially offset from the longitudinal center of said insertion tube.

12. The endoscope according to claim 11 further including:
    a sheath surrounding said insertion tube;
    a tubing coupled to said sheath; and
    a channel in said insertion tube, the longitudinal bending axis being in said channel.

13. An endoscope insertion tube having a steerable tip comprising:
    a handle;

an insertion tube coupled to said handle, said insertion tube including a plurality of members hingedly coupled to each other by a first and second set of hinges, the axis of rotation of a first set of hinges and the axis of rotation of said second set of hinges crossing at a point radially offset from the longitudinal center of said insertion tube.

14. The endoscope according to claim 13 further including a channel and said crossing point is located within said channel.

15. The endoscope according to claim 14 further including a biopsy tubing assembly within said channel, instantaneous bending center being located within said biopsy tubing for permitting said biopsy tubing to be radially offset from said longitudinal center of said insertion tube and maintain a constant length while said insertion tube is bent.

16. The endoscope according to claim 15 further including a visual display means within said insertion tube.

17. The endoscope insertion tube according to claim 14 further including:
 a first set of cable means including at least two cables from said handle to said tip portion;
 a second set of cable means including at lest two individual cable means extending from said handle to said tip portion;
 a first control rod for moving said first set of cable means: and
 a second control rod coupled to said second set of cable means for moving the individual cable means in opposite directions when said control rod is moved in a first direction.

18. The endoscope according to claim 17 further including a mechanical couple between said second control rod and said first set of cable means for moving said second set of cable means when said first control rod is moved.

19. The endoscope according to claim 17 wherein said control rod is rotated in said first direction.

20. An endoscope having a steerable tip portion at a distal end of an insertion tube comprising:
 a handle coupled to a first end of said insertion tube;
 control means for steering said tip portion;
 a plurality of members hingedly coupled to each other, forming said steerable tip portion;
 a first cable extending from said control means to said steerable tip portion, said first cable being a first distance radially from a longitudinal bending center of said tip portion; and
 a second cable extending from said control means to said steerable tip portion, said second cable being a second distance radially from a longitudinal bending center of said tip portion, said second distance being greater than said first distance.

21. The endoscope insertion tube according to claim 20, further including a third cable extending from said handle to said steerable tip portion, said third cable being said first distance radially from said longitudinal bending center of said tip portion and a fourth cable extending from said handle to said steerable tip portion, said fourth cable being said second distance radially from said longitudinal bending center of said tip portion, said first and second cables forming a pair for steering said tip portion in a first plane of movement and said third and fourth cables forming a pair for steering said tip portion in a second plane of movement.

22. An endoscope comprising:
 a handle housing having first and second control rods;
 an insertion tube having a steerable distal tip portion for insertion into the human body, said insertion tube coupled to said handle housing;
 a first set of cable means coupled to said first control rod and extending to said tip portion of said insertion tube for steering said tip portion in a first plane of movement, said first set of cable means moving when said first control rod is moved a selected distance;
 a second set of cable means coupled to said second control rod and extending to said tip portion of said insertion tube for steering said tip portion in a second plane of movement; and
 a mechanical coupling means between said first control rod and said second cable means for causing said second set of cable means to move when said first control rod is moved said selected distance.

23. The endoscope according to claim 22, further including a mechanical coupling means between said second control rod and said first cable means for causing said first set of cable means to move a selected distance when said second control rod is moved.

24. The endoscope according to claim 22 wherein each of said cable means includes a cable and a housing around said cable.

25. The endoscope according to claim 22 wherein said mechanical coupling between said first control rod and said second cable means includes a cam coupled to said first control rod and a cam follower coupled to said housing of said second cable means for moving said second housing relative to said second cable.

26. The endoscope according to claim 22 wherein rotating said control rods steers said tip portion.

27. The endoscope according to said claim 22 wherein said mechanical coupling means includes gears.

28. The endoscope according to claim 27 wherein said first control rod is coupled to said second cable means through a plurality of ring gears and bevel gears, said bevel gears being coupled to said ring gears for rotation about an axis perpendicular to the axis of rotation of said ring gears.

29. The endoscope according to claim 22 wherein said first set of cable means includes only a single cable means in said first set.

30. The endoscope according to claim 22 wherein said second set of cable means includes at least two cable means.

31. The endoscope according to claim 22 wherein said first control rod extends through said second control rod.

32. The endoscope according to claim 22 wherein said first set of cable means includes two cables and rotating said first control rod causes each cable in said first cable means to move said opposite direction of unequal length from each other and said second cable means to move the same distance as each other.

33. A method of steering an endoscope insertion tube tip comprising:
 retracting a first cable a first selected distance; and
 extending a second cable a second selected distance; said second selected distance being greater than said first selected distance for causing said insertion tube to bend about an axis different from a longitudinal central axis.

34. The method according to claim 33, further including the step of retracting a housing surrounding a third cable simultaneously while said first and second cables are being retracted and extended respectively.

35. A method of controlling an endoscope insertion tube comprising:
retracting a first cable a first selected distance;
retracting a second cable said first selected distance; and
extending a third cable a second selected distance, said second selected distance being different from said first distance.

36. The method of moving a biopsy tube relative to an insertion tube comprising:
fixing a distal end of said biopsy tube to a distal end of said insertion tube;
moving said insertion tube longitudinal center a first distance; and
moving a longitudinal center of said biopsy tube a second distance, different than said first distance while permitting said biopsy tube to move relative to said insertion tube.

37. The method according to claim 36 wherein said biopsy tube stretches and contracts as said insertion tube is moved.

38. An endoscope comprising:
an insertion tube for inserting into a human body, said insertion tube having an instantaneous bending center which is radially offset from its longitudinal axial center;
a handle coupled to said insertion tube, said handle remaining outside said human body, said insertion tube being rotatably coupled to said handle for rotation about the longitudinal axis of said insertion tube;
a tubing extending from a tip portion of said insertion tube, exiting at an end region of said insertion tube; and
a control member means for permitting a user to selectively rotate said insertion tube about its longitudinal axis while maintaining said handle in a stationary position.

39. The apparatus according to claim 38, wherein said tubing includes a biopsy tubing, electrical wires, and other medical devices, extending from the tip of said insertion tube to said handle.

40. The endoscope according to claim 38, further including:
a pair of cables extending from said controls, through said insertion tube and to said tip portion, said pair of cables providing steering in a single plane of movement independent of the angular position attained by rotating said insertion tube with said control member, the combination of rotational steering by rotating said insertion tube using said pair of cables permitting said tip portion to be steered into any desired quadrant within the body.

41. The endoscope according to claim 38, further including:
a first set of cable means for extending from said controls to said tip portion for steering said endoscope, in a first plane of movement; and
a second set of cable means extending from said controls to said tip portion for steering said endoscope, in a second plane of movement.

* * * * *

UNITED STATES PATENT AND TRADEMARK OFFICE
CERTIFICATE OF CORRECTION

PATENT NO. : 4,947,827

DATED : August 14, 1990

INVENTOR(S) : Eric Opie et al.

It is certified that error appears in the above-identified patent and that said Letters Patent is hereby corrected as shown below:

In claim 2, column 21, line 67, after "claim" please insert --1--.

In claim 6, column 22, line 20, please delete "aid" and substitute therefor --said--.

Signed and Sealed this

Twenty-sixth Day of November, 1991

Attest:

HARRY F. MANBECK, JR.

*Attesting Officer*  *Commissioner of Patents and Trademarks*